(12) United States Patent
Wilusz et al.

(10) Patent No.: US 6,852,531 B2
(45) Date of Patent: Feb. 8, 2005

(54) COMPOSITIONS AND METHODS FOR REPRODUCING AND MODULATING MAMMALIAN MESSENGER RNA DECAPPING

(75) Inventors: Jeffrey Wilusz, Lebanon, NJ (US); Carol Wilusz, Lebanon, NJ (US); Min Gao, San Diego, CA (US)

(73) Assignee: University of Medicine & Dentistry of NJ, New Brunswick, NJ (US)

( * ) Notice: Subject to any disclaimer, the term of this patent is extended or adjusted under 35 U.S.C. 154(b) by 0 days.

(21) Appl. No.: 09/955,462

(22) Filed: Sep. 18, 2001

(65) Prior Publication Data

US 2002/0150913 A1 Oct. 17, 2002

Related U.S. Application Data

(60) Provisional application No. 60/233,682, filed on Sep. 19, 2000.

(51) Int. Cl.[7] .................................................. C12N 5/08
(52) U.S. Cl. .............................. 435/367; 435/4; 435/6; 435/183; 435/325; 435/366; 536/22.1; 536/23.1; 536/24.1
(58) Field of Search ............................. 536/22.1, 23.1, 536/24.1; 435/4, 6, 183, 325, 366, 367

(56) References Cited

PUBLICATIONS

Ohno et al. A nuclear cap binding protein from HeLa cells. Dec. 1990. Nucleic Acids Research 18(23): 6989–6995.*

Hellmann et al. A polypeptide which reverses cap analogue inhibition of cell–free protein synthesis. Purification and binidng to capped oligonucleotides. Apr. 1982. Journal of Biological Chemistry 257(8): 4056–4062.*

Robyt et al. Biochemical techniques: Theory and Practice. 1987 Brooks/Cole Publishing Company. pp. 263, 264 and 271.*

Rainen et al. Antibodies distinguishing between intact and alkali–hydrolyzed 7–methylguanosine. Nucleic Acids Research 5: 3877–3889, 1978. Abstract only.*

Tucker & Parker, *Mechanism and Control of mRNA Decapping in Saccharomyces cerevisiae*, Annu. Rev. Biochem. 69:571–95 (2000).

Holcik & Liebhaber, *Four Highly Stable Eukaryotic mRNAs Assemble 3'Untranslated Region RNA–Protein Complexes Sharing Cis and Trans Components*, Proc. Natl. Acad. Sci. U.S.A. 94:2410–2414 (1997).

Morley & Hershey, *A Fractionated Reticulocyte Lysate Retains High Efficiency for Protein Synthesis*, Biochimie. 72:259–264 (1990).

Merrick, *Translation of Exogenous mRNAs in Reticulocyte Lysates*, Meth. Enzymol. 101: 606–615 (1983).

* cited by examiner

*Primary Examiner*—James Ketter
*Assistant Examiner*—David Lambertson
(74) *Attorney, Agent, or Firm*—Hoffman & Baron, LLP

(57) ABSTRACT

An in-vitro system in which mammalian messenger RNA decapping occurs is provided, for use in identifying modulators, deficiencies, and other aspects of the regulation of RNA turnover.

30 Claims, 20 Drawing Sheets

COMPOSITIONS AND METHODS FOR REPRODUCING AND MODULATING MAMMALIAN MESSENGER RNA DECAPPING

CROSS REFERENCE TO RELATED APPLICATION

This application claims priority under 35 U.S.C. 119(e) from U.S. Ser. No. 60/233,682, filed Sep. 19, 2000, which is incorporated herein by reference in its entirety.

GOVERNMENTAL SUPPORT

The research leading to the present invention was supported, at least in part, by Grant Nos. GM58276, GM6382-01, and CA80062 from the National Institutes for Health. Accordingly, the Government may have certain rights in the invention.

BACKGROUND OF THE INVENTION

The steady state level of a messenger RNA (mRNA) is a function of its rate of synthesis and degradation. Just as numerous differences in the rate of synthesis (i.e., transcription) exist, so to do differences in relative mRNA stability. Messenger RNAs with very short half-lives include many clinically important transcripts, namely transcription factors, growth factors and cytokines. Messenger RNAs with extremely long half-lives also have been described, including globin transcripts. In addition, messenger RNAs from some disease alleles contain an inappropriately placed nonsense codon resulting in premature termination of the open frame encoding the protein product. These "nonsense codon-containing" mRNAs are degraded very rapidly in cells. Clearly, mRNA stability plays an important regulatory role in the molecular biology of the cell.

Since mRNA stability plays a key role in regulated gene expression, it is a natural target for drug development. This potential for drug development is further enhanced when one surveys some of the best described cases of regulated mRNA stability. First, the importance of modulation of the immune system is central to many aspects of clinical medicine. Several genes that play a key role in immunologic responses and development (e.g. cytokines) are clearly regulated at the level of mRNA stability. Second, the expression of several proteins that play regulatory roles in the cell cycle are also regulated at the level of mRNA stability. This observation implies that mRNA stability may influence cancer treatments, for example regulation of mRNA turnover can control the expression of a variety of growth factors and proto-oncogenes. Finally, all aspects of gene therapy would benefit from a better understanding of modulating influences of mRNA stability. Messenger RNA stability, therefore, remains an unexploited target for drug development with a great deal of potential.

Messenger RNAs contain a poly(A) tail of approximately 200 bases at their 3' end when they are synthesized. The first step in the pathway of turnover of mRNAs in mammalian cells appears to be the stepwise removal of the tail by a process called deadenylation. The rate of deadenylation, as well as the overall rate of turnover of the mRNA, is influenced by sequence elements present in the mRNA. The best characterized of these elements to date is an "AU rich" element located in the 3' untranslated region of the mRNA body. The presence of an AU rich element in a mRNA causes a dramatic increase in the rate of deadenylation/degradation, effectively shortening the half-life of a mRNA. After the poly(A) tail is shortened to a minimal length, the body of the transcript is rapidly degraded with no apparent intermediates. Certain aspects of the foregoing are described in co-pending application Ser. No. 09/320,609, filed May 26, 1999, incorporated herein by reference in its entirety.

In the yeast *Saccharomyces cerevisiae*, deadenylated mRNAs are usually degraded by two major pathways. In the predominant pathway, deadenylated mRNAs are decapped and degraded by a 5'-to-3' exonuclease. If this pathway is blocked by genetic mutations, an alternative pathway can be observed in which deadenylated mRNAs are degraded by a 3'-to-5' exonuclease.

It is not known how mammalian mRNAs are degraded in cells following their deadenylation nor how the process is regulated. Only one study has been performed to date that suggests the possibility that mammalian mRNAs can be decapped in vivo. This study, however, used an indirect highly-sensitive PCR assay that may not have detected true intermediates in the mRNA degradation pathway. There is currently no direct biochemical evidence for decapping in mammalian cells. The putative human homologue of the yeast decapping enzyme Dcp1p surprisingly does not possess detectable decapping activity and has recently been identified as a transcription factor.

The lack of mechanistic detail in the model for mRNA turnover presented above reflects the lack of a good experimental approach to study the process. Human cells and mammals in general do not represent a genetic system that is easily exploited using current technology. The key to understanding mechanisms of gene expression in cells from higher organisms, therefore, lies in a biochemical approach. When used in conjunction with reagents developed from chemical or molecular approaches, such systems can provide the backbone of assays to understand and exploit aspects of cellular biology for therapeutic advantages.

Decapping is a major regulated step in the turnover of yeast mRNAs. It is a key regulatory element in mammalian cells as well. As shown herein, AU-rich instability elements stimulate decapping efficiency. Several other elements have been identified in mammalian mRNAs that stabilize transcripts. A 51 base pyrimidine-rich element has been identified in the relatively stable alpha-globin mRNA that is responsible for its extremely long half-life in vivo. As shown herein, such stability elements also regulate decapping efficiency. Regulation of mRNA decapping, therefore, plays an important role in the post transcriptional regulation of gene expression.

It is toward the development of an in vitro system in which mammalian messenger RNA decapping occurs and can be exploited for the screening of decapping modulators, for identifying species-specific decapping enzymes and associated factors, among other uses, that the present invention is directed.

The citation of any reference herein should not be construed as an admission that such reference is available as "Prior Art" to the instant application.

SUMMARY OF THE INVENTION

In one broad aspect, the invention is directed to a composition comprising:
  a) a mammalian cell cytoplasmic extract;
  b) a methylated cap analog; and
  c) a cap-labeled mRNA substrate.

The composition provides the necessary components for observing decapping of mammalian mRNA in vitro. The mammalian cell cytoplasmic extract may be, for example, an S100 extract comprising 100,000×g, 1 hour supernatant from a mammalian cell lysate, the cells obtained from mammalian cells or tissue, including cell culture. In one embodiment, HeLa cells (human cervical cancer cell line) are used. The extract may be prepared by dialysis of a said extract containing 10% glycerol. An S100 extract is one example of an extract, and is useful in each embodiment of this invention, although other mammalian cell cytoplasmic extracts are also contemplated.

The methylated cap analog may be, for example, $^{7me}$G-pppG or $^{7me}$GTP.

The cap-labeled mRNA substrate may be detectably labeled at the alpha phosphate of the cap, and may be a label such as a radioactive label, a non-radioactive isotopic label, a fluorescent moiety, a visibly-detectable moiety, a releasable substrate or a co-factor for a chemical or enzymatic reaction. The cap-labeled mRNA substrate may include poly(A) or at least one RNA element which can be an instability element, such as an AU-rich element, or a stability element, such as a pyrimidine-rich element.

In another embodiment, the aforementioned composition may be used to additionally detect mRNA deadenylation and degradation. The mammalian cell cytoplasmic extract may be depleted of activity of proteins that bind polyadenylate.

In a further embodiment, the invention is directed to a kit for in-vitro mammalian mRNA decapping containing at least:
a) a mammalian cell cytoplasmic extract; and
b) a methylated cap analog.

The kit may further include a cap-labeled mRNA substrate, for example, one labeled at the alpha phosphate of the cap. The label may be a radioactive label, a non-radioactive isotopic label, a fluorescent moiety, a visibly-detectable moiety, a releasable substrate or a co-factor for a chemical or enzymatic reaction.

In another embodiment, the mammalian cell cytoplasmic extract may be depleted of activity of proteins that bind polyadenylate.

The invention is also directed to a method for carrying out in vitro mammalian mRNA decapping including at least the steps of
a) providing any of the compositions as described above containing at least a mammalian cell cytoplasmic extract, a cap analog and a cap-labeled mRNA substrate;
b) incubating the composition at about 30° C. for about 30 min and monitoring decapping by detection of release of label from said cap-labeled RNA.

In another embodiment, a method is provided for identifying a compound as a modulator of mammalian mRNA decapping comprising carrying out the above method in the presence and absence of said compound, and correlating any change in decapping by the presence of said compound with modulator activity of said compound.

In either of the foregoing methods, the cap-labeled mRNA substrate may include poly(A) or at least one RNA element which can be an instability element, such as an AU-rich element, or a stability element, such as a pyrimidine-rich element.

Also part of this invention is a polypeptide with the following unique combination of properties: a molecular weight of about 50 to about 100 kilodaltons (kD) in molecular exclusion chromatography; precipitation by 20% ammonium sulfate, elution at between about 440 to 500 mM NaCl from a heparin-Sepharose column, and the ability to decap mammalian RNA. A polynucleotide encoding the polypeptide and antibody which binds to the polypeptide are also contemplated.

These and other aspects of the present invention will be better appreciated by reference to the following drawings and Detailed Description.

BRIEF DESCRIPTION OF THE DRAWINGS

FIG. 1. Identification of a decapping activity in HeLa cytoplasmic extracts.

FIG. 2. Methylated cap, analog specifically activates decapping in HeLa cytoplasmic extracts by sequestering cap-binding proteins.

FIG. 4. The addition of poly(A) competitor RNA specifically activated decapping of polyadenylated RNA substrates.

FIG. 5. The presence of an AU-rich element significantly stimulates the efficiency of decapping.

DETAILED DESCRIPTION OF THE INVENTION

Figure 1A:
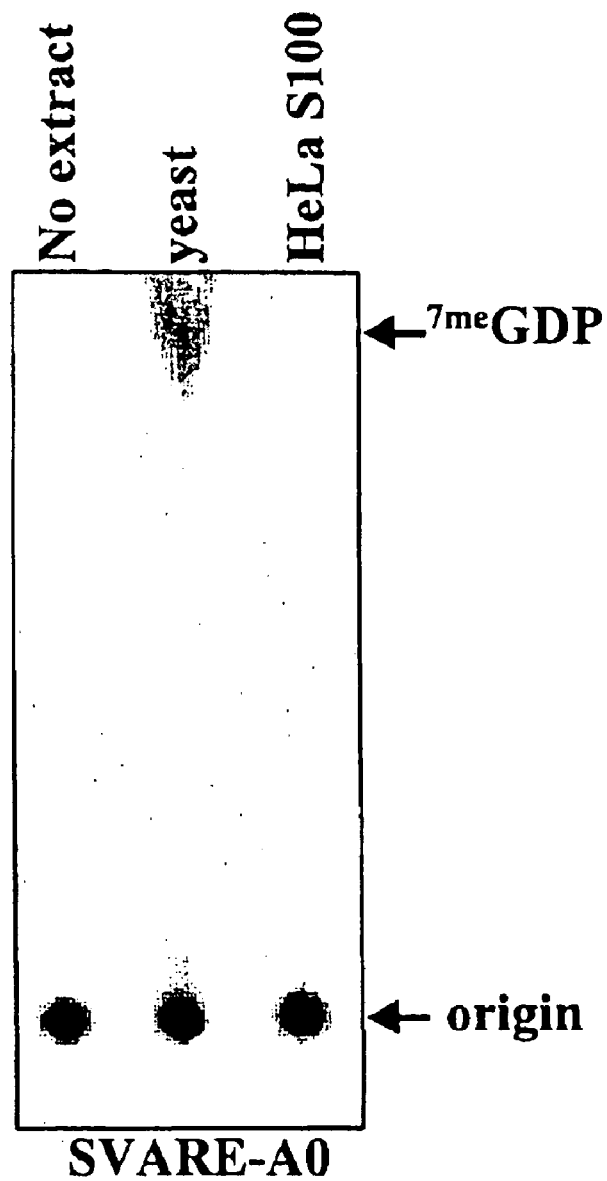
FIG. 1A. SVARE-A0 RNA, radiolabeled exclusively at the alpha-phosphate of the 5' cap structure, was incubated in standard decapping conditions using no extract, S. cerevisiae whole cell extract (yeast lane), or HeLa S100 cytoplasmic extract. The $^{7me}$GDP product of the decapping reaction was resolved by thin layer chromatography on PEI cellulose sheets developed using 0.45 M ammonium sulfate. The identification of radioactive spots was determined using markers that were visualized by UV shadowing.

Numerous terms and phrases are used throughout the instant Specification. The meanings of these terms and phrases are set forth below.

In particular, as used herein "half-life" of an RNA molecule refers to the measurement of the decline in the amount of an RNA molecule.

As used herein "turnover" refers to the degradation of an RNA molecule. Turnover comprises deadenylation and degradation.

As used herein a "cap" or "5' cap" or "terminal cap", can be used interchangeably, and refer to a 7-methyl guanosine (7meG) cap chemically conjugated to the most 5' nucleotide of the RNA molecule. The 5'-most phosphate on the RNA will be referred to herein as the "alpha phosphate".

As used herein, the term "stability" refers to the maintenance of an RNA molecule so that it can function, and thus retard the degradation process of an RNA molecule.

An "RNA element" is a base sequence the possession of which makes an mRNA resist degradation (stability element) or vulnerable to degradation (instability element). Such an element may also be defined as a base sequence to which proteins bind which either contribute to or reduce mRNA degradation.

As used herein, the phrase "polyadenylic acid (poly(A)) tail" refers to a string of contiguous adenylic acids (polyadenylate) added post transcriptionally to the 3' end of an RNA molecule, such as mRNA.

As used herein, the phrase "a polyadenylic acid competitor nucleic acid oligomer" refers to an oligomer comprising contiguous adenylic acids" which can be added to a system of the invention and sequester proteins that bind poly(A). Thus, the degradation of a particular RNA molecule having a poly(A) tail can be modulated.

Also, as used herein, the phrase "restriction endonuclease" refers to an enzyme that recognizes specific nucleotide sequences in a nucleic acid molecule, and produces a double-stranded break within or near the site. Some restriction enzymes, such as EcoRI or HindIII produce "complementary tails" on each of fragments produced. These tails are said to be "sticky" because under hybridization conditions they can reanneal with each other. Thus, if two separate nucleic acid molecules share the same restriction site, then both will contain complementary single-stranded tails when treated with the same restriction endonuclease, and can be spliced together forming a recombinant nucleic acid molecule.

Naturally, as used herein, the phrase "restriction endonuclease site" refers to a specific nucleotide sequence that is recognized by a specific restriction endonuclease.

Furthermore, numerous conventional molecular biology, microbiology, and recombinant DNA techniques within the skill of the art can be readily utilized to practice the instant invention. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of a nucleic acid molecule, such as DNA or RNA, that can be inserted into a vector at specific restriction sites. The segment of the nucleic acid molelcule may encode a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "polynucleotide" or "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The terms polynucleotide and nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5', to 3' direction along the nontranscribed strand of DNA (i.e., the strand having a sequence homologous to the mRNA). A "recombinant DNA molecule" is a DNA molecule that has undergone a molecular biological manipulation.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The inventors herein have discovered a novel enzyme in cytoplasmic extracts from mammalian cells that specifically removes the 5' cap structure from mRNAs. Heretofore unrecognized and unappreciated in a mammalian system, an in-vitro system has been developed therefrom in which this 'decapping activity' may be regulated by a variety of elements in the messenger RNA (RNA elements), including AU-rich elements and pyrimidine-rich elements, that are known to play a key role in determining the relative half life of transcripts. Thus, the effects of the various components in the system, particularly the target mRNA itself, may be studied in detail using the methods of the invention. The availability of the mammalian decapping system of the invention enables for the first time several useful activities such as but not limited to 1) high throughput screening of compounds/macromolecules that affect the decapping of mammalian mRNAs in order to design drugs to affect the expression of selected transcripts; 2) purification, characterization and cloning of proteins and enzymes involved in mRNA decapping, such proteins and enzymes being potential pharmacologic agents or targets; 3) the development as a diagnostic aid for determining the molecular defect in selective disease alleles; 4) development of in vitro mRNA decapping systems for other eukaryotic organisms, such as parasites, for which the identification of differences between the mammalian and non-mammalian decapping can lead to novel drug discovery; and 5) improving gene delivery systems by using the system of the invention to identify factors and RNA sequences that affect RNA stability at the level of decapping. These uses are merely exemplary and non-limiting, and will be described in more detail below.

The mammalian in vitro mRNA decapping system comprises the following basic components, each of which may be substituted for by like alternates, as described further below:

1) a mammalian cell cytoplasmic extract;
2) a methylated cap analog; and
3) a cap-labeled RNA substrate.

The cap-labeled RNA substrate may also contain a poly (A) tail, RNA elements, etc.

The mammalian cytoplasmic extract may be derived, for example, from HeLa S3 cells, but it is not so limited, and may be prepared by clearing of ribosomes and other organelles from a cytoplasmic extract from the cells using a standard protocol such as that described by Dignam et al., 1983, Accurate transcription initiation by RNA polymerase II in a soluble extract from isolated mammalian nuclei, Nucleic Acids Res 11(5):1475–1489, with the following modifications: (1) extracts are adjusted to 10% glycerol prior to dialysis to maintain the activity of the components and (2) dialysis times are reduced to 30 min. for similar reasons. Other ways to maintain stability of the extract are readily used and fully embraced herein, and the term "cell cytoplasmic extract" is inclusive of the various means of preparing a polysome-free, high-speed supernatant prepared from lysed mammalian cells. An example of such an extract is an S100 extract. An extract which is as free of ribosomes as possible within the compass of methods known in the art is preferred.

The methylated cap analog may be, by way of non-limiting example, $^{7me}$GpppG or $^{7me}$GTP. Any methylated cap analog may be used in this invention. Other examples of methylated cap analogs are 7meGpppA, 7meGpppC, 7meGpppU, in which the A, C, and U may be unmethylated or methylated in one or more positions. These are known reagents which may be synthesized by conventional methods or obtained commercially, for example, from Amersham Pharmacia Biotech (see also Darzynkiewicz, Nucleosides Nucleotides 18:1125–1126 (1999).

The cap-labeled RNA substrate (which may also contain a poly(A) tail, instability elements, etc) may be any capped mRNA substrate for which decapping activity may be measured. In a non-limiting example, the mRNA is labeled at the alpha phosphate of the cap. The label may be a radioactive or non-radioactive isotopic label, or any other detectable group which does not interfere with the decapping system, such as but not limited to a fluorescent moiety (i.e., a fluorigenic substrate), a visibly-detectable moiety (a chromogenic substrate), or a releasable substrate or co-factor for a chemical or enzymatic reaction. These examples are merely exemplary and non-limiting, as the assay format may be designed to be carried out by other manual, semiautomatic or automatic procedures, the latter useful in particular for high-throughput screening.

The foregoing components of the decapping system may be assembled in a variety of ways to achieve the decapping in vitro. Generally, the following components are present, the volumes and concentrations variable depending on the particular assay:

1 microliter of a solution of a methylated cap analog (50–500 ng/microliter);

1 microliter cap-labeled RNA (~5–200 fmol);

4 microliters mammalian cell S100 extract; and 4 microliters water.

The mixture is incubated at about 30° C. for about 30 min; aliquots are then taken at designated time points to follow the kinetics of decapping by visualization of the product of decapping, $^{7me}$GDP, from the cap-labeled RNA.

Once the parameters of a particular decapping assay are determined, the assay may be simplified and fewer time points measured, or a baseline and single time point may be measured. A simplified assay permits a large number assays to be performed concurrently.

In one embodiment of a manual procedure, the components are as follows (referred to herein as "standard reaction conditions"):

1 microliter $^{7me}$GpppG or $^{7me}$GTP competitor (50–500 ng/microliter);

1 microliter RNA (~5–200 fmol; labeled at the alpha phosphate of the cap);

4 microliters S100 extract; and 4 microliters water.

The mixture is incubated at 30° C. for 30 min; aliquots are then taken at designated time points to follow the kinetics of decapping by visualization of the product of decapping, $^{7me}$GDP, by, for example, thin layer chromatography on a cellulose PEI sheet using a mobile phase of 0.45 M ammonium sulfate. Other means for identifying the decapping product are fully embraced herein.

As will be shown in the examples herein and the accompanying figures, the methylated cap analog, $^{7me}$GpppG or $^{7me}$GTP in the examples above, is a key reagent to achieve mRNA decapping in vitro. As seen in the examples below, standard S100 extracts from human cells exhibit no decapping. The addition of cold $^{7me}$GpppG or $^{7me}$GTP, however, activates the human cytoplasmic extract and allows one to observe decapping in real time. The titration of methylated cap analogs into the system results in the removal of cap binding proteins from 5' end of capped RNA substrates incubated in the system. Furthermore, decapping is shown to be negatively influenced by a poly(A) tail on RNA substrates. mRNAs are not decapped in vivo until they are deadenylated, that is until their poly(A) tails are significantly shortened.

A confirmation that the in-vitro decapping system of the invention is truly reproducing in vivo observations is shown by the effect of a poly(A) tail on RNA substrates incubated in the assay of the invention should be a strong negative influence on decapping. As seen in the example, this is precisely the case. Thus, the system of the invention is accurately reproducing processes that occur inside the cell.

Figure 9:
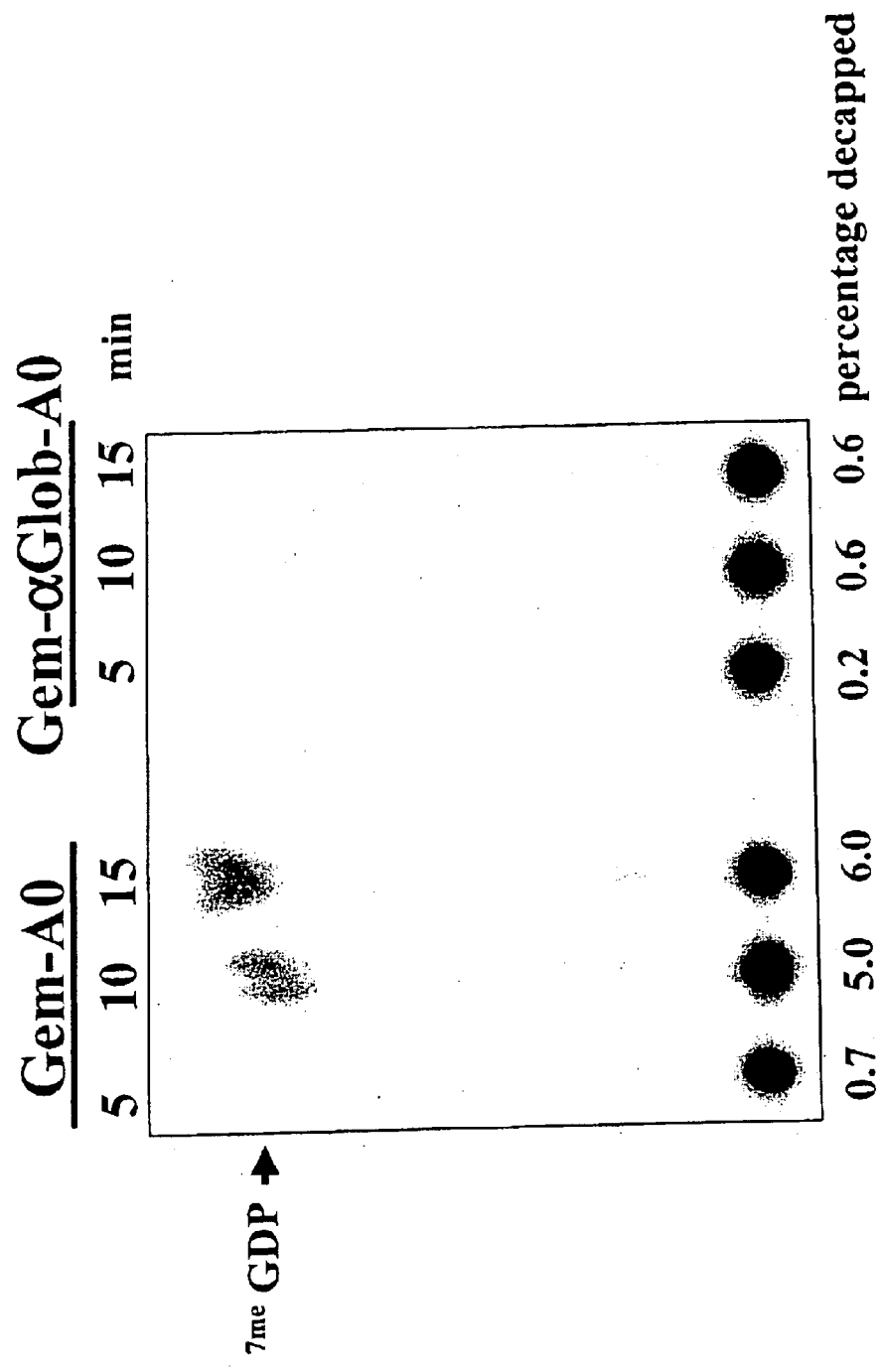
FIG. 9: The mRNA stabilizing element from the alpha-globin gene represses decapping in vitro. Cap labeled GemA0 RNA or a variant containing the 51 base alpha-globin stability element (Gem-aGlob-A0) were incubated in the in vitro decapping system for the times indicated. 7meGDP reaction products were separated by thin layer chromatography and visualized and quantitated by phosphorimaging.

Decapping of RNAs in the system is regulatable by RNA elements. The best characterized mRNA stability element is an AU-rich sequence. The existence of AU-rich elements is known in the art. (See, for example, Chen and Shyu (1995); Shyu and Kamen (1986); Shyu, et al. (1991); Shyu, et al. (1989); and Wilson and Treisman (1988)). Proteins which interact with these elements are also known (see for example Brewer (1991); Fan and Steitz (1998); Lai, et al. (1999); Levine, et al. (1993); Loflin, et al. (1999); Ma, et al. (1996); Peng, et al. (1998). The presence of this element in an mRNA in results in a dramatic destabilization of the transcript in vivo. The addition of such an element, for example an AU-rich element from the TNF-alpha mRNA into the RNA substrates results in a dramatic increase in the rate of decapping. The AU-rich element from the GMCSF mRNA also results in a dramatic increase in the rate of decapping in the system. The in vitro decapping assay accurately reproduces cellular regulatory influences and may thus be used identify the regulatory mechanisms and learn how to manipulate them in therapeutic interventions. Similarly, a pyrimidine-rich element, for example such an element which is approximately 50 bases in length, acts as a stability element by significantly decreasing decapping activity. Thus the presence of this element in an mRNA results in stabilization of the transcript in vivo. Addition of such an element, for example the 51 base pyrimidine-rich element from alpha-globin mRNA, results in a dramatic decrease in the rate of decapping, e.g. up to a 10-fold decrease in decapping efficiency (FIG. 9). The existence of pyrimidine-rich elements is known in the art (see for example Chkheidze A N, Lyakhov D L, Makeyev A V, Morales J, Kong J, Liebhaber S A. Assembly of the alpha-globin mRNA stability complex reflects binary interaction between the pyrimidine-rich 3' untranslated region determinant and polyC binding protein alphaCP. Mol Cell Biol. 1999 19:4572–81; Liebhaber S A.mRNA stability and the control of gene expression. Nucleic Acids Symp Ser. 1997;(36):29–32; Russell J E, Morales J, Makeyev A V, Liebhaber S A. Sequence divergence in the 3' untranslated regions of human zeta- and alpha-globin mRNAs mediates a difference in their stabilities and contributes to efficient alpha-to-zeta gene development switching.Mol Cell Biol. 1998 18:2173–83; Holcik M, Liebhaber S A. Four highly stable eukaryotic mRNAs assemble 3' untranslated region RNA-protein complexes sharing cis and trans components. Proc Natl Acad Sci USA. 1997 94:2410–4; Russell J E, Morales J, Liebhaber S A.The role of mRNA stability in the control of globin gene expression.Prog Nucleic Acid Res Mol Biol. 1997;57:249–87; and Weiss I M, Liebhaber S A. Erythroid cell-specific mRNA stability elements in the alpha 2-globin 3' nontranslated region. Mol Cell Biol. 1995 15:2457–65).

The invention is also directed to kits for carrying out mRNA decapping comprising at least a mammalian cell cytoplasmic extract and a methylated cap analog. The extract may be prepared in 10% glycerol prior to dialysis, to maintain stability. Optionally included with the kit, or provided separately, is a detectably-cap-labeled mRNA substrate. Other components and instructions may be included.

The cell extract of the present invention is prepared from lysed mammalian cells or tissues. Various methods known to the skilled artisan may be used to prepare the cell extract. Various sources of cells may be used, including fresh cells and tissues, and cells lines. Such cells may comprise foreign nucleic acid, such as in cells that are infected; or are transiently or stably transfected with a mammalian expression vector, the latter as described in more detail below. Furthermore, prior to preparation of the cell extract, cells may be exposed to certain chemical or other extracellular stimuli, for example, hormones, growth factors, and kinase and phosphatase inhibitors, which may alter RNA decapping, for which subsequent studies as described herein may be used to identify the induction of certain proteins involved in modulating RNA decapping, or for the identification of agents which may counteract adverse RNA decapping modulation induced by such stimuli. The cell extract is preferably free of nuclei and nuclear contents and comprises cytoplasm, but this is not essential unless particular components, such as enzymes or other factors, from nuclei, interfere with the operation of the system. In a typical preparation (for example an S100 extract), which may be modified without departing from the scope of the invention, cells are grown, harvested, lysed, centrifuged for 100,000×g for 1 hour, and dialyzed. Glycerol may be added to protect the extract if stored frozen. Variations in the preparation of a 100,000×g mammalian cell supernatant may be undertaken which provides a suitable component for the system of the invention, and such variations are fully embraced herein (for example an extract centrifuged at a different rate or time, such as 99,000×g, etc.).

Cells useful for the preparation described herein include immortalized or partially immortalized mammalian cells which can be grown in large amounts under defined conditions, such as HeLa cells and various T-cell cell lines. Other sources include tissues, blood cells, or myeloid cells. Other sources are well within the realm of the present invention.

Also part of this invention is a polypeptide with the following unique combination of properties: a molecular weight of about 50 to about 100 kilodaltons (kD) in molecular exclusion chromatography; precipitation by 20% ammonium sulfate, elution at between about 440 to 500 mM NaCl from a heparin-Sepharose column, and the ability to decap mammalian RNA. In one embodiment, this polypeptide causes decapping of a cap-labelled mRNA substrate when combined with a methylated cap analog. This polypeptide is therefore called a "decapping enzyme". The decapping enzyme may be used in various ways suggested by this invention. For example, the enzyme may be used to target specific mRNAs for degradation by attaching to the enzyme a nucleic acid sequence which hybridizes to the mRNA. When hybridization occurs, the enzyme will then act to decap the mRNA, leading directly to its degradation. This enzyme targeting system is particularly useful for degrading mRNAs which translate into defective or otherwise undesirable proteins, or simply to regulate the levels of certain proteins. As is apparent from this discussion, such a system also is useful as a research tool for drug discovery. An addition, the decapping enzyme may itself be used to probe cell extracts for other factors which bind to it in nature and therefore regulate its activity, providing additional guidance on targeting the decapping enzyme to specific mRNAs.

The polypeptide of this invention may be obtained by known methods, such as chemical synthesis, or by recombinant DNA techniques, a recombinant DNA technique being one in which a polynucleotide coding for said polypeptide is added to a host cell so as to result in the expression of the polypeptide. The polypeptide can be purified away from host cell proteins by such methods as immunoprecipitation with antibodies and by other standard protein purification techniques such as electrophoresis in one or two dimensions and chromatography. The polypeptide of this invention may also be isolated from tissue or cells which naturally express it, or from cultured cells which express it, such as HeLa cells. Such isolation employs known methods of isolating proteins followed by assays and purification steps as described below to obtain the polypeptide of this invention with its defining characteristics.

A polynucleotide which encodes the polypeptide of this invention is also contemplated. Such a polynucleotide, when expressed in a conventional expression system as described below, expresses a polypeptide with the following unique combination of properties: a molecular weight of about 50 to about 100 kilodaltons (kD) in molecular exclusion chromatography; precipitation by 20% ammonium sulfate, elution at between about 440 to 500 mM NaCl from a heparin-Sepharose column, and the ability to decap mammalian RNA. The polynucleotide of this invention may be used, in one aspect, to obtain the polypeptide of this invention.

Monoclonal and polyclonal antibodies which bind to the polypeptide of this invention, preferably with high affinity and specificity, are also contemplated. Such antibodies are raised by known methods, such as hybridoma technology in the case of monoclonal antibodies, and collection from an immunized laboratory animal in the case of polyclonal antibodies. Thus an antibody which binds specifically and with high affinity to a polypeptide having a molecular weight of about 50 to about 100 kilodaltons (kD) in molecular exclusion chromatography, precipitating with 20% ammonium sulfate, eluting at between about 440 to 500 mM NaCl from a heparin-Sepharose column, and the able to decap mammalian RNA is part of this invention. By binding specifically is meant the conventional meaning of binding to the polypeptide of this invention and showing no significant binding to other antigens. High affinity is also used here in the sense that it is generally understood in the art. The antibodies of this invention may be used as research tools in drug discovery, and in addition may be used for example to prevent mRNA degradation by blocking the action of the decapping enzyme. The antibodies may also be used analytically and diagnostically, for example to determine levels of decapping enzyme in a particular cell or tissue.

As described above, a cell used to prepare the cell extract may comprise foreign DNA, and can be prepared as described below. A polynucleotide of this invention can be obtained and/or expressed using a large number of vector-host systems known in the art. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the polynucleotide into a cloning vector which has complementary cohesive termini. However, if the complementary restriction sites used to fragment the polynucleotide are not present in the cloning vector, the ends of the molecule may be enzymatically modified. Alternatively, any site desired may be produced by ligating nucleotide sequences (linkers) onto the termini of the polynucleotide; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the polynucleotide are generated. Preferably, the cloned polynucleotide is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

Naturally, any of the methods previously described for the insertion of an isolated polynucleotide into a cloning vector may be used to construct expression vectors containing a polynucleotide consisting of appropriate transcriptional/translational control signals and the protein coding sequences. These methods may include in vitro recombinant DNA and synthetic techniques and in vivo recombination (genetic recombination).

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible metallothionein IIa gene promoter, hygromycin selectable marker: Invitrogen), pREP8 (BamHI, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, *supra*) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Once a particular polynucleotide is inserted into a vector, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few. In addition, a host cell strain may be chosen which modulates the expression of the inserted sequences, or modifies and processes the gene product in the specific fashion desired to express the polypeptide of this invention.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The target, cap-labeled mRNA sequence in the system of the present invention may be any one of a number of RNA or modified RNA molecules. For example, synthetic RNA may be prepared by solid phase synthesis, or reproduced by in-vitro transcription using phage polymerase as is known to the skilled artisan. Naturally occurring RNA may be isolated from cells, tissues, and other biological sources. Cap-labelling may be achieved by methods known in the art.

The particular mRNA used in the system and methods of the present invention may be selected depending on the particular species of mRNA to be studied. Investigations of mRNA turnover, endogenous modulators of its turnover and exogenously added molecules, particularly small molecules which affect mRNA turnover, have important therapeutic implications in the prophylaxis and treatment of a variety of conditions and diseases. Certain mRNAs are short-lived, such as those of cytokines; others are long-lived, such as globin message. The regulation of mRNA lifetimes for particular proteins and particular cell types may be subject to various adverse effects, from infection to external stimuli, which alter the turnover and hence cellular physiology. In various conditions, altered expression of cellular proteins and cellular phenotypes may be consequences of altered mRNA turnover. Pharmacological intervention of such altered mRNA turnover, to restore an altered turnover, or the induction of an altered turnover to achieve a benefit to the organism, are achievable based upon the systems and methods described herein. For example, a particular mRNA, such as that of the proinflammatory cytokine TNF-alpha, is selected as a target for identification of small molecule modulators that may decrease the turnover by affecting decapping, and this prolong the lifetime, and expression, of this protein by inflammatory cells. Such modulators may provide substantial benefit in the treatment of certain immunological diseases wherein an increased secretion of TNF-alpha is beneficial. Conversely, massive overproduction of TNF-alpha in sepsis, or its adverse effects in rheumatoid arthritis and inflammatory bowel disease may be ameliorated by use of an agent which further increases the turnover and thus decreases the expression of TNF-alpha by inflammatory cells.

The application of the invention herein to other mRNA species is embraced by the teachings herein. In particular, the methods of the present invention facilitate high throughput screening for the identification of modulators of RNA decapping, to be applied to the treatment or prophylaxis of disease.

Furthermore, the cap-labeled mRNA molecule may be detectably labeled using routine protocols readily known to a skilled artisan. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. Capped RNAs are preferably labelled with alpha-$^{32}$P GTP. When a control marker is employed, the same or different labels may be used for the receptor and control marker. In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available detection may be accomplished by any of the presently utilized calorimetric, spectrophotometric, fluorospectrophotometric, amperometric or gasometric techniques known in the art. In a further example, biotin moieties may be incorporated into the RNA cap by any number of means. Subsequently, the biotinylated RNA or degradation fragments may be quantitated by an avidin reagent.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in Methods in Enzymology, 70. 419–439, 1980 and in U.S. Pat. No. 4,857,453.

Thus, the assay of the invention which achieves mammalian mRNA decapping in vitro is useful for a variety of studies, such as but not limited to identifying the components involved in decapping, identifying cells or tissues with defects in decapping and possible pharmaceutical agents that can restore activity, the identification of inhibitors of decapping, screening of molecules that modulate decapping activity, to name but a few examples. The decapping assay of the invention can be combined with reagents used to measure mRNA stability, such as deadenylation and/or degradation, in order provide a system in which the entire process of mRNA turnover is assessed in a single container. Thus, the compositions and kits described above may also include reagents for carrying out additional aspects of RNA turnover.

Thus, a method is also provided for identifying an agent capable of modulating the decapping of a target mRNA sequence comprising (A) preparing the decapping system of the present invention;

(B) introducing said agent into said system; and (C) correlating any effect of the agent on decapping with modulation of the decapping of said target RNA sequence in said system.

A further method is provided for identifying a defect in a mammalian cell cytoplasmic extract (such as an S100 extract) responsible for altered decapping activity in a certain cell or tissue comprising:

(A) preparing the system of the present invention using a mammalian cell cytoplasmic extract (such as an S100 extract) from a particular cell or tissue; and (B) monitoring the extent of decapping of said target RNA sequence in said system.

The foregoing method is useful in identifying a defect present in a cell or tissue. Components may be added to the foregoing system to attempt to circumvent the block in normal decapping activity.

The inventors herein have identified and characterized a novel regulated decapping activity in mammalian cytoplasmic extracts which plays a key role in mRNA turnover. Decapping was found to be repressed by two activities: cap binding proteins and poly(A) binding proteins. Decapping was found to be directly stimulated by AU-rich elements, and directly inhibited by pyrimidine-rich elements. The compositions and systems of the invention may include such decapping activity modulators as baseline components or the target mRNA from which to study or identify modulators of decapping as altered by the presence of these elements.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

A. Materials and Methods for Performing Experimental Procedures

1. RNAs

SVARE-A0 RNA, which contains the 34 base AU-rich element from TNF-alpha inserted into the BamHI—BclI fragment representing the 3' portion of SV40 late mRNAs, was transcribed from HindIII linearized templates as previously described (Ford et al., 1999). SVARE-A60 RNA, a variant that contains a 60 base poly(A) tract at its 3' end, was prepared as previously described (Ford et al., 1999). Gem-A60 RNA, which contains sequences from the pGem4 polylinker region followed by 60 A residues, was prepared as previously described (Ford et al., 1999). GemARE-A60, a variant that contains the 34 base AU-rich element from TNF-alpha, was prepared as described previously (Gao et al., 2000). Transcription of Hind III linearized templates yields GemARE-A0 RNA. Sequences encoding a 60 base poly(A) tail were added to DNA using a ligation-PCR approach previously described (Ford et al., 1997). The template for GM-CSF and GMCSF (−ARE) was pGM-CSF (Shaw and Kamen, 1986) cut with EcoRI (to yield a 750 base transcript) or NcoI (to yield a 515 base transcript) respectively. GMCSFT-A0 RNA was prepared by inserting the AU-rich element from TNF-alpha into pGMCSF by inserting the oligonucleotide 5'-CATGATTATTTATTATTT ATTTATTATTTATTTATTTAAAC (SEQ ID NO:1) and its appropriate complement at its NcoI site. This replaced the endogenous destabilizing element of GMCSF with the TNF-alpha AU-rich element. Transcription of NcoI linearized templates yields a 557 base GM-CSFT-A0 RNA. The addition of a 60 base poly(A) tail to GM-CSFT A0 RNA was performed by ligation-PCR as described above.

RNAs were transcribed in vitro using SP6 polymerase as described previously (Wilusz and Shenk, 1988) in the absence of cap analog and radioactive rNTPs. To label RNAs exclusively at their cap structures, transcription products were then capped using recombinant vaccinia guanyltransferase and alpha-$^{32}$P-GTP (Zhang et al., 1999b). All RNAs were purified on 5% acrylamide gels prior to use. To make RNAs that were radioactively labeled at the alpha-phosphate of an unmethylated cap, S-adenosyl homocysteine was substituted for S-adenosyl methionine in the capping reaction.

Synthetic RNAs used in competition studies were made by the NJMS Molecular Core Facility and contained the following sequences: ARE: 5'AUUAUUUAUUAUUUAUU UAUUAUUUAUUUAUUUA SEQ ID NO:2); Non-specific competitor: 5'-GGAUUAACUAAUUGAUACCGCGUAU ACACGCGG (SEQ ID NO:3). Poly(A) and poly(C) competitor RNAs, along with $^{7me}$GpppG and GpppG were purchased from Amersham Pharmacia Biotech.

2. Extracts

Whole-cell yeast extracts were prepared as described (Lin et al., 1985). S100 cytoplasmic extracts were prepared from HeLa spinner cells grown in 10% horse serum as described previously (Ford et al., 1999; Ford and Wilusz, 1999). Aliquots were stored at −80° C.

3. In vitro Decapping Assay

Decapping assays were performed using conditions adapted from Zhang et al (1999b). 10–50 fmoles of cap-labeled RNAs were incubated with 4 microliters HeLa S100 cytoplasmic extract in a 10 microliter reaction in the presence of CE buffer (50 mM Tris pH 7.9, 30 mM $(NH_4)_2SO_4$, 1 mM $MgCl_2$) and 20 micromolar cap analog (where indicated). Reaction mixtures were incubated at 30° C. for the times indicated and stopped by the addition of 1 microliter of 0.25 M EDTA. Reaction products were separated and identified by thin layer chromatography on PEI cellulose sheets developed in 450 mM $(NH_4)_2SO_4$. Quantitation was performed using a Molecular Dynamics Phosphorimager. Twenty micrograms of $^{7me}$GMP and $^{7me}$GDP were routinely spotted on TLC plates along with reaction samples to serve as markers that could be visualized by UV shadowing.

4. UV Cross-Linking

UV cross-linking analysis was performed as described (Wilusz and Shenk, 1988). Briefly, 20–50 fmoles of cap-radiolabeled RNA was incubated in the in vitro decapping assay for 5 min. and then reaction mixtures were irradiated on ice for 10 min. using a 15W germicidal light. RNases A and T1 were added and proteins covalently attached to short radioactive RNA oligomers were analyzed on a 10% acrylamide gel containing SDS. For analysis of UV cross-linked DAN/PARN protein by immunoprecipitation using a polyclonal antibody obtained from M. Wormington (Korner et al., 1998), 400 ul of NET2 buffer (50 mM Tris pH 7.6, 150 mM NaCl, 0.01% NP40) was added to reaction mixtures following RNase treatment and reaction mixtures were centrifuged for 4 min. Pre-cleared samples were incubated on ice with 2–5 microliters of specified rabbit polyclonal antisera for 1 hr. Antigen antibody complexes were collected on protein A-positive *Staphylococcus aureus* cells, washed five times in RIPA buffer (50 mM Tris, pH 7.6, 150 mM NaCl, 0.1% SDS, 1% NP40, 0.5% deoxycholate), and immunoprecipitated cross-linked proteins were analyzed on a 10 or 15% acrylamide gel containing SDS.

B. Experimental Procedures and Results

1. Identification of a Decapping Activity in HeLa Cytoplasmic Extracts

Following deadenylation, most yeast mRNAs are decapped prior to degradation by the 5'-to-3' exonuclease Xrn1p (Muhlrad et al., 1994). Whether decapping plays a major role in the turnover of mammalian mRNAs following poly(A) tail shortening is unclear. No direct biochemical evidence exists for a bona-fide Dcp1p-like decapping enzyme in mammalian cells. In order to obtain a decapping activity in mammalian extracts, the decapping assay was used to study the yeast enzyme (Zhang et al., 1999b). Briefly, RNA substrates were exclusively labeled at the alpha-phosphate of the cap structure using recombinant vaccinia capping enzyme and alpha-$^{32}$P-GTP and incubated in cytoplasmic extracts in the presence of $Mg^{2+}$. Reaction products were spotted directly onto PEI cellulose sheets and small molecules were resolved in 450 mM ammonium sulfate. The positions of $^{7me}$GMP, $^{7me}$GDP and $^{7me}$GTP were identified by UV shadowing of markers run in each lane. As seen in FIG. 1A, yeast whole cell extracts contain a potent decapping activity that produces a significant amount of $^{7me}$GDP from cap-labeled RNA substrates. The $^{7me}$GDP product of decapping, however, was not detected when cap-labeled RNAs were incubated in HeLa S100 extracts. In addition, no significant decrease in radioactivity at the origin was observed in these experiments. Thus the decapping activity of HeLa cells is somehow masked in the in vitro assay.

Figure 1B:
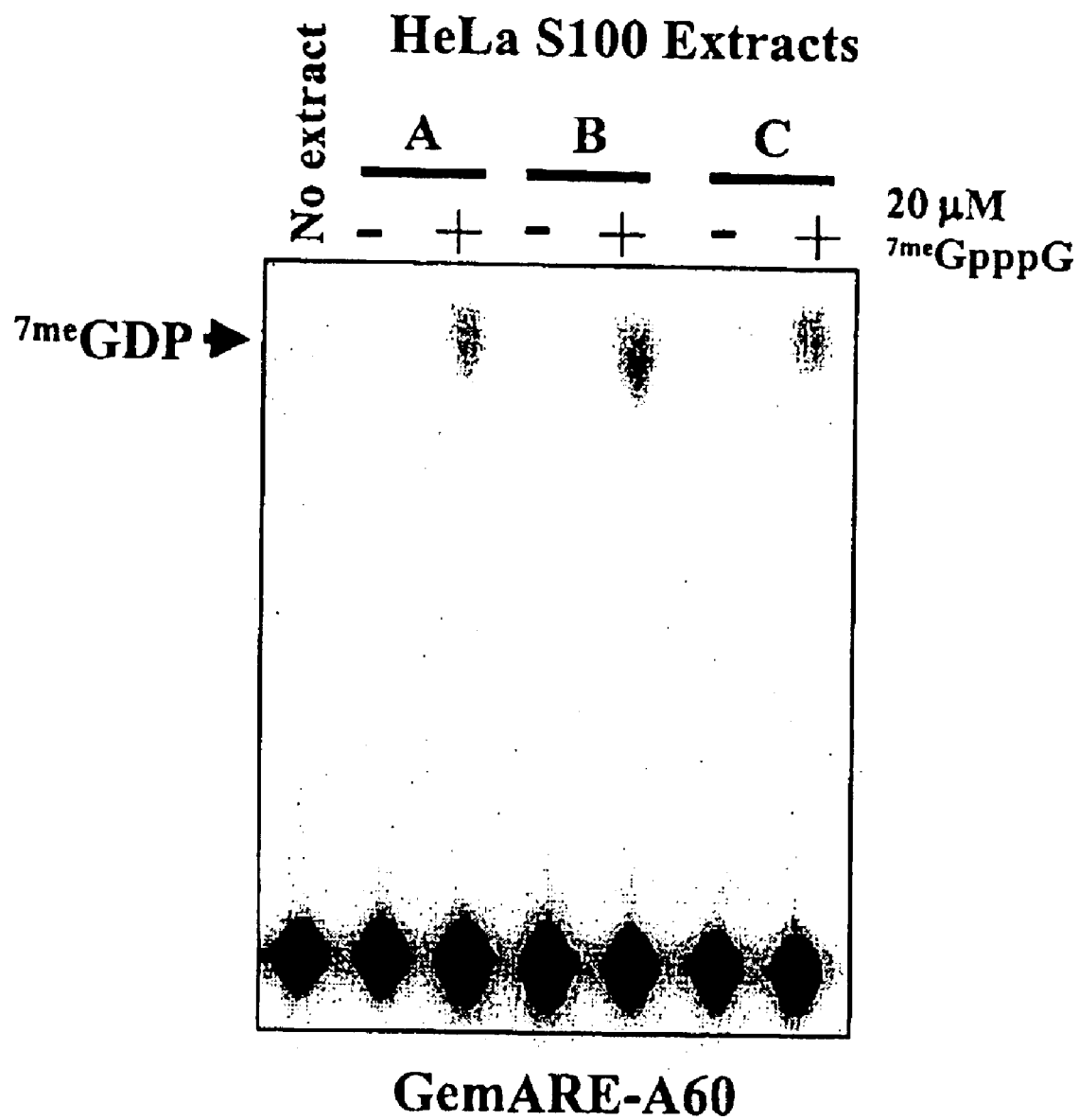
FIG. 1B. GemARE-A60 RNA, radiolabeled exclusively at the alpha-phosphate of the 5' cap structure, was incubated in the absence of extract (no extract lane) or in the presence of three independently prepared S100 cytoplasmic extracts from HeLa cells (A, B,or C) either in the absence (−lanes) or presence of 20micromolar cap analog (+lanes). The $^{7me}$GDP product the decapping reaction was resolved by chromatography on PEI cellulose sheets developed using 0.45 M ammonium sulfate.
Figure 3A:
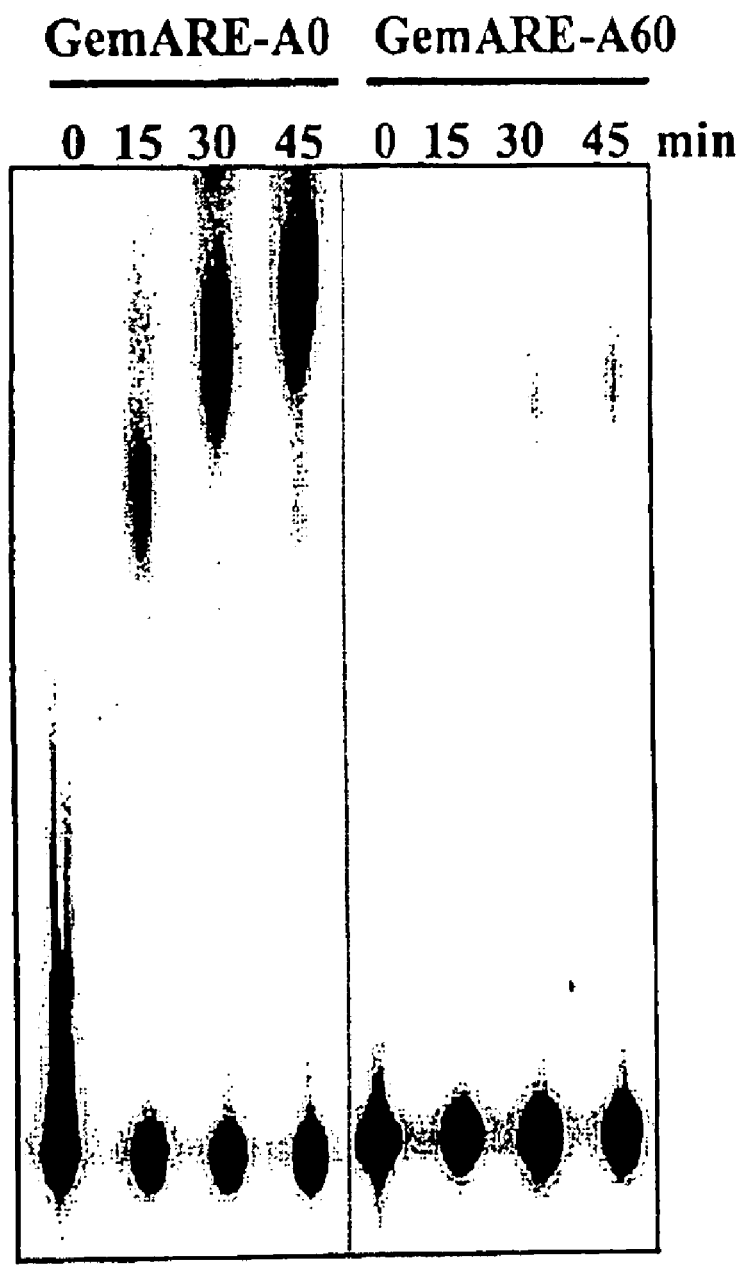
FIG. 3. The presence of a poly(A) tail represses decapping of three independent RNA substrates. Equimolar amounts of three independent, cap-labeled RNA substrates that either lacked a poly(A) tail (GemARE-A0 (FIG 3A), SVARE-A0 (FIG. 3B), and GM-CSF-A0 (FIG. 3C) or contained 60 adenylate residues at their 3' end (GemARE-A60 (FIG. 3A), SVARE-A60 (FIG. 3B and GM-CSFT-A60 (FIG. 3C)) were incubated in the in vitro decapping assay in the presence of cap analog. Aliquots were removed at the indicated time points and reaction products were analyzed by thin layer chromatography on PEI cellulose sheets.
Figure 3B:
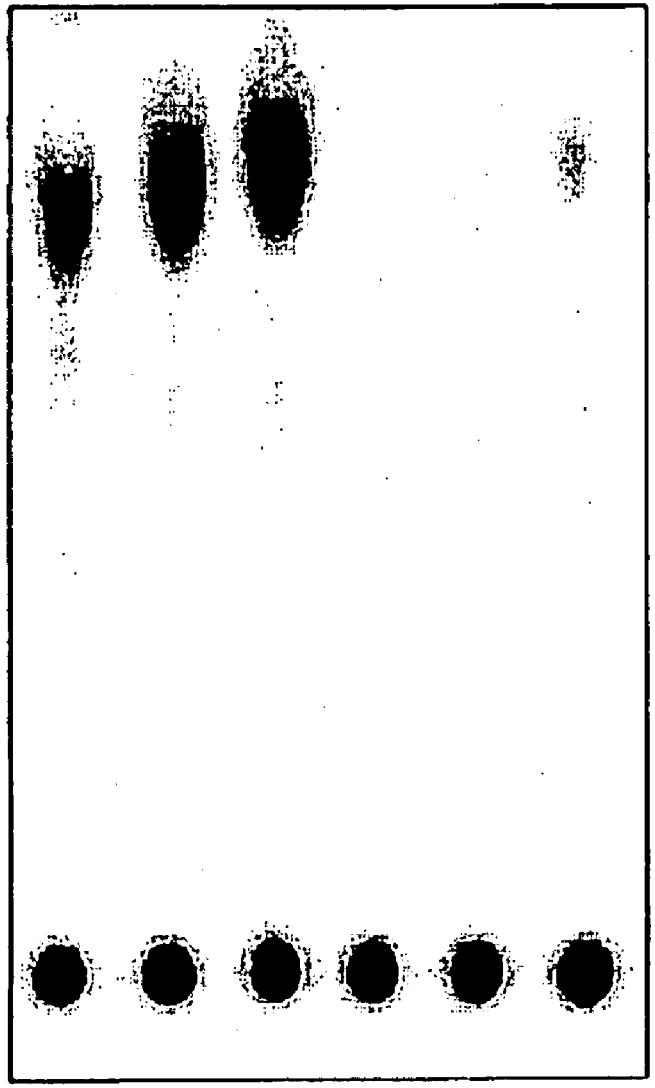
Figure 3C:
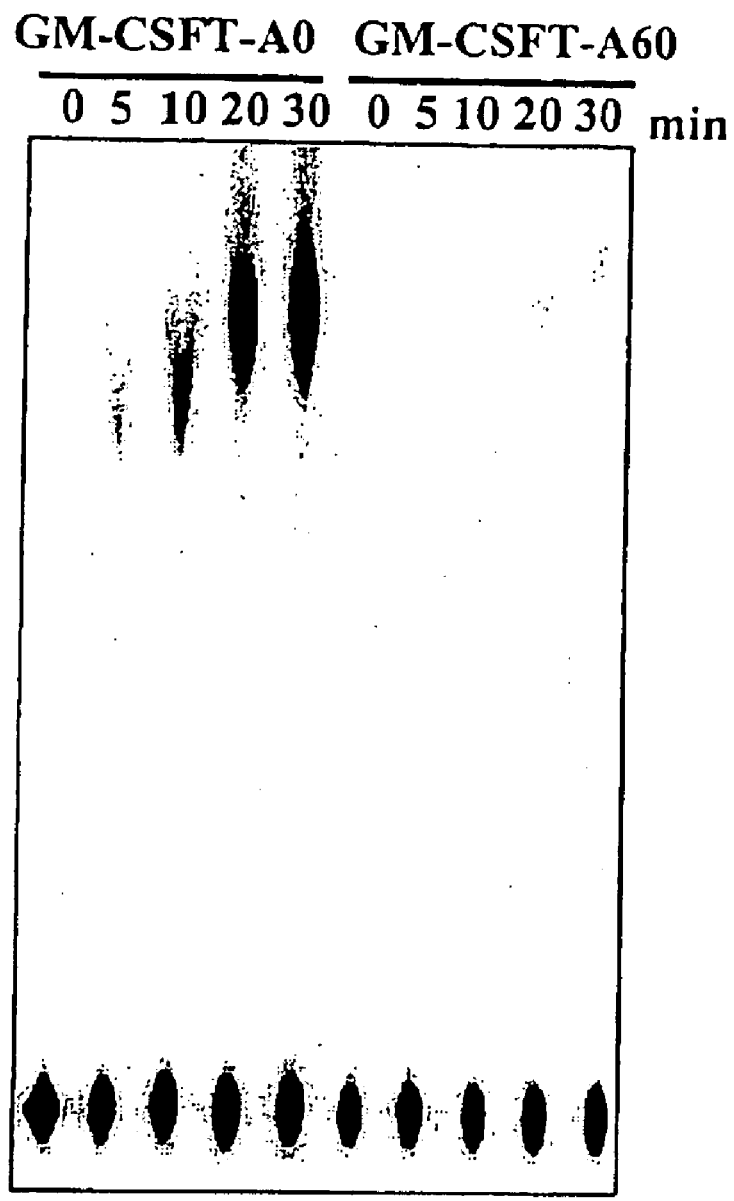
Figure 5A:
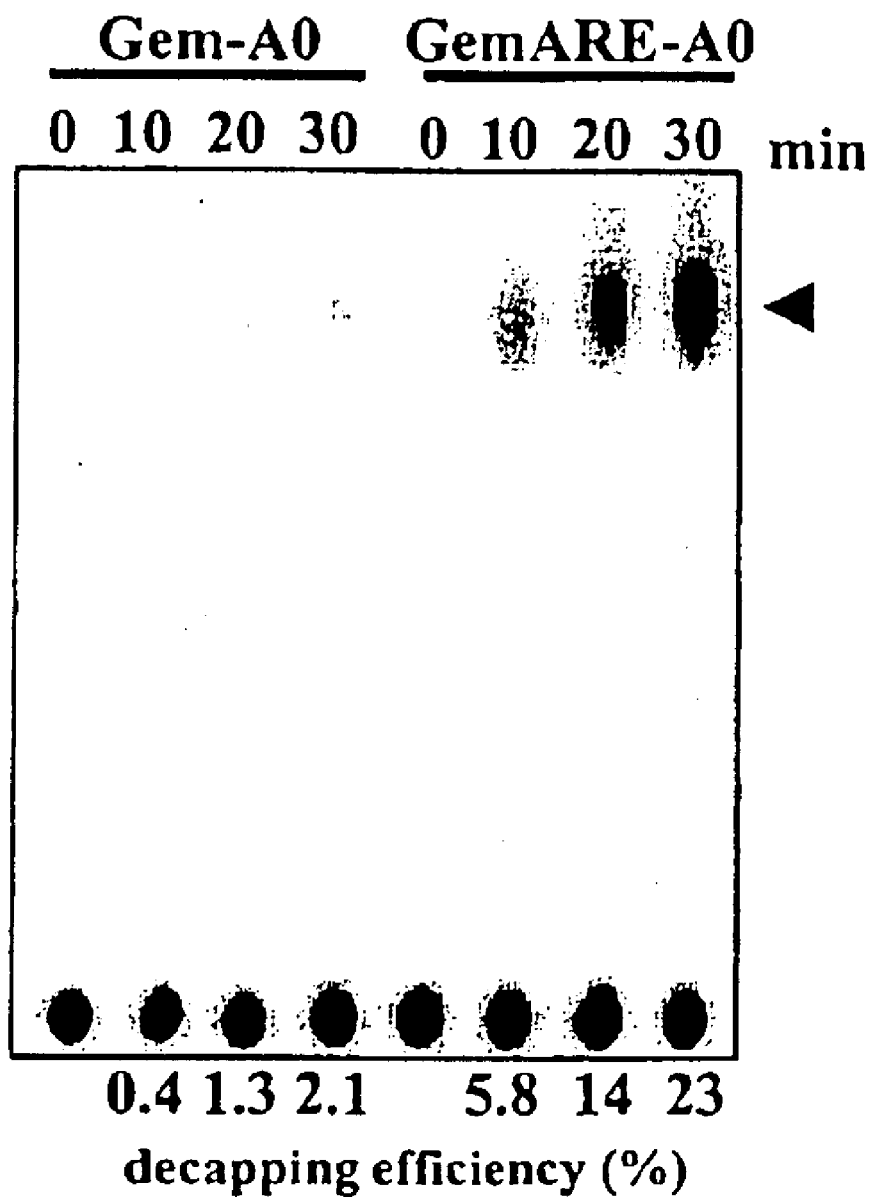
FIG. 5A.
Figure 5B:
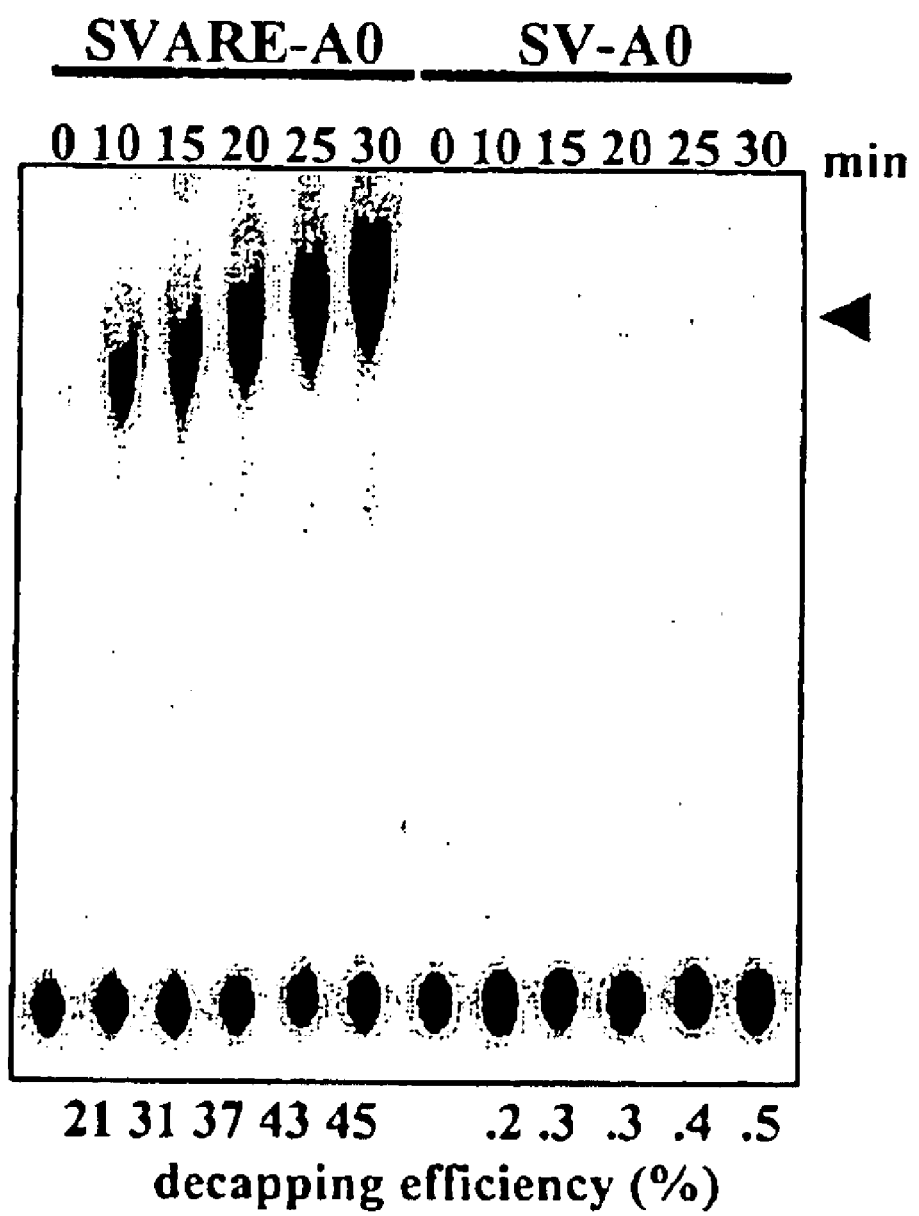
FIG. 5B. A matched pair of cap-labeled RNA substrates that either lacked (Gem-A0 or SV-A0) or contained the TNF-alpha AU-rich element (GemARE-A0 or SVARE-A0) were incubated n the in vitro decapping system in the presence of cap analog for the indicated amount of time. Reaction products were analyzed by thin layer chromatography on PEI cellulose sheets.

The cap structure of mRNA substrates becomes inaccessible when the transcript is incubated in HeLa extracts due to competing cap-binding activities such as eIF4E (Sonenberg et al., 1978) or the deadenylase DAN/PARN (Dehlin et al., 2000; Gao et al., 2000). Parker and colleagues have previously shown that the yeast decapping enzyme Dcp1p is not inhibited by small cap analogs (LaGrandeur and Parker, 1998). The addition of $^{7me}$GpppG cap analog to extracts selectively sequesters these competing cap-binding activities without inhibiting the mammalian decapping enzyme. A decapping activity in HeLa extracts was found by adding 20 micromolar $^{7me}$GpppG to reaction mixtures and repeating the decapping assay using 3 independently prepared HeLa cytoplasmic extracts. As seen in FIG. 1B, the addition of cap analog activated decapping of RNA substrates in all of the extracts tested as seen by the accumulation of $^{7me}$GDP. The activation of decapping on all RNA substrates we have tested required the addition of cap analog. Furthermore, decapping occurred with linear kinetics, was dependent on the presence of $Mg^{2+}$, and did not require ATP (FIGS. 3 and 5). Finally, the decapping activity was highly specific for $^{7me}$Gppp capped RNAs, as unmethylated cap structures were not detectably cleaved in the assays (FIG. 1C). Taken together, these data show that HeLa cytoplasmic extracts contain a decapping activity that is repressed by cap binding proteins which prevent its access to the cap of RNA substrates.

Figure 2A:
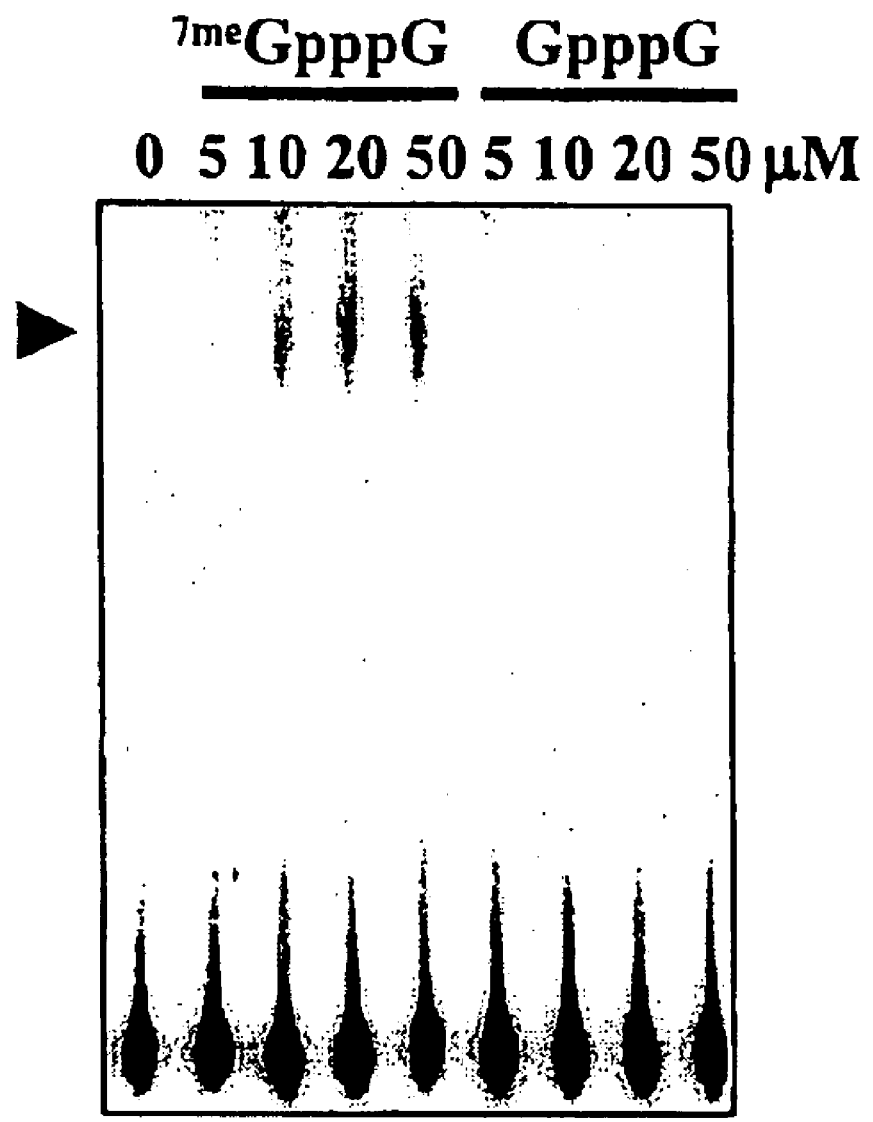
FIG 2A. The indicated amounts of $^{7me}$GpppG or GpppG were incubated with HeLa S100 extracts and decapping assays were performed using cap-labeled GemARE-A60 RNA. The products of decapping were analyzed on PEI-cellulose sheets. The arrowhead indicates $^{7me}$GDP.
Figure 2B:
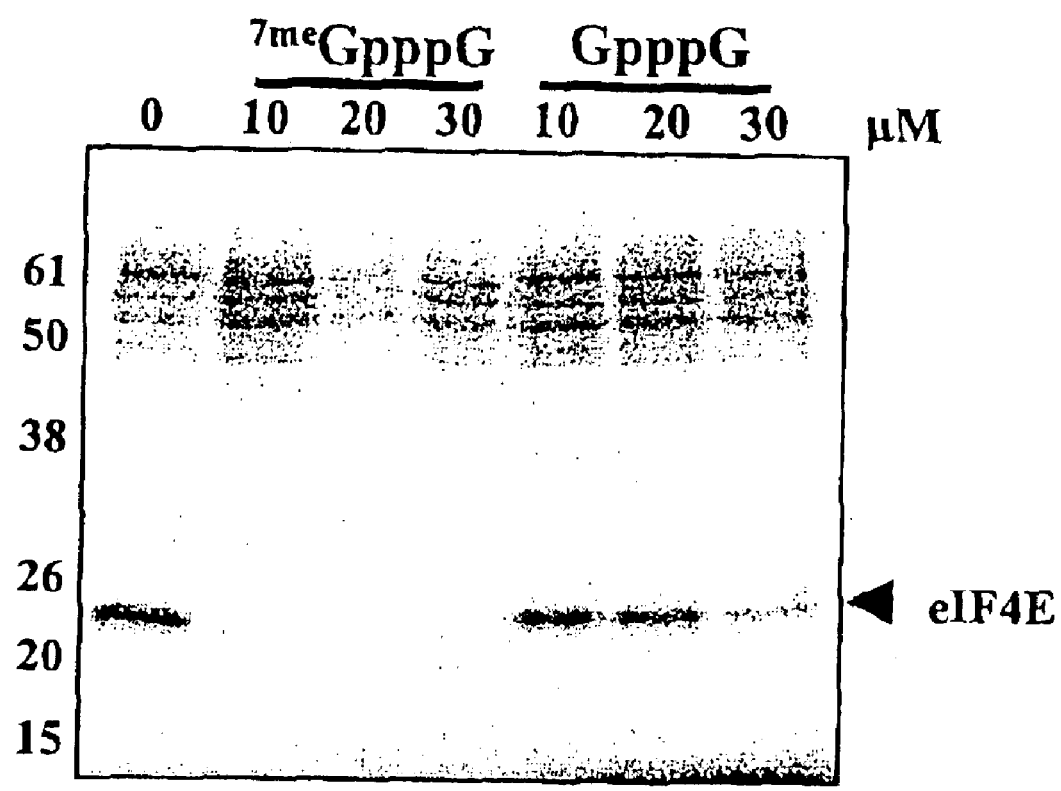
FIG. 2B. The indicated amounts of $^{7me}$GpppG or GpppG were incubated in HeLa S100 extracts using cap-labeled GemARE-A6 RNA under decapping conditions. After 5 mm., UV cross-linking was performed, mixtures were treated with ribonuclease, and proteins radiolabeled through cross-linking to cap-labeled RNA oligomers were analyzed by electrophoresis on a 15% acrylamide gel containing SDS. The position of eIF4E is indicated by the arrowhead.
Figure 2C:
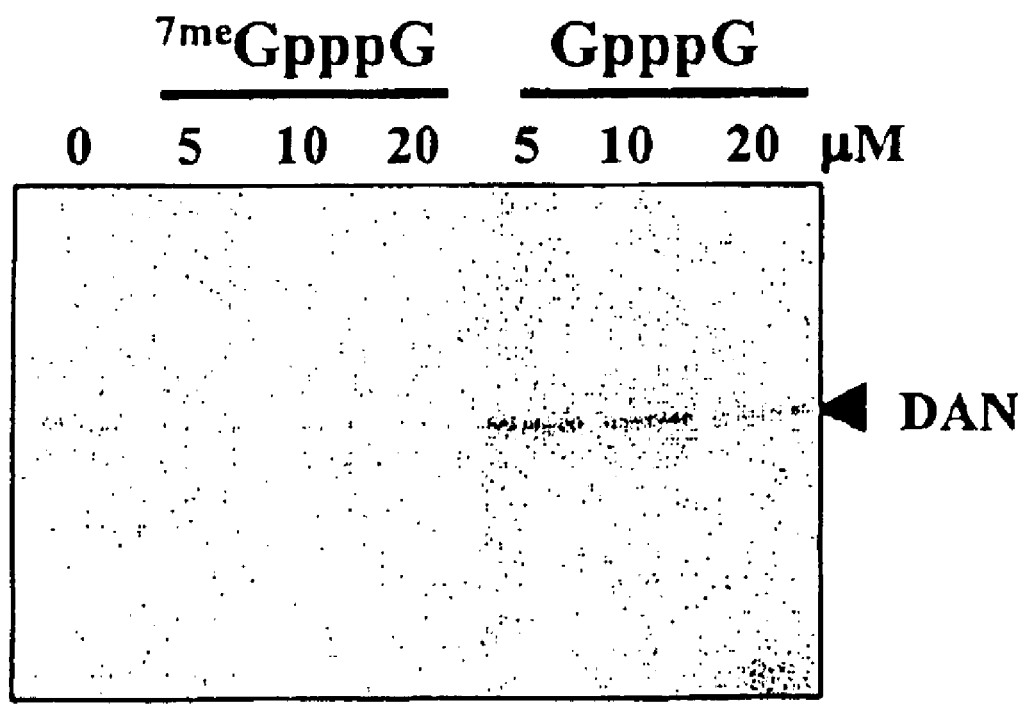
FIG. 2C. The indicated amounts of $^{7me}$GpppG or GpppG were incubated HeLa S100 extracts using cap-labeled GemARE-A60 RNA under decapping conditions. After 5 min., UV cross-linking was performed, mixtures were treated with ribonuclease, DAN/PARN proteins radiolabeled through cross-linking to cap-labeled RNA oligomers were immunoprecipitated and analyzed by electrophoresis on a 10% acrylamide gel containing SDS. The position of DAN/PARN is indicated by the arrowhead.
Figure 2D:
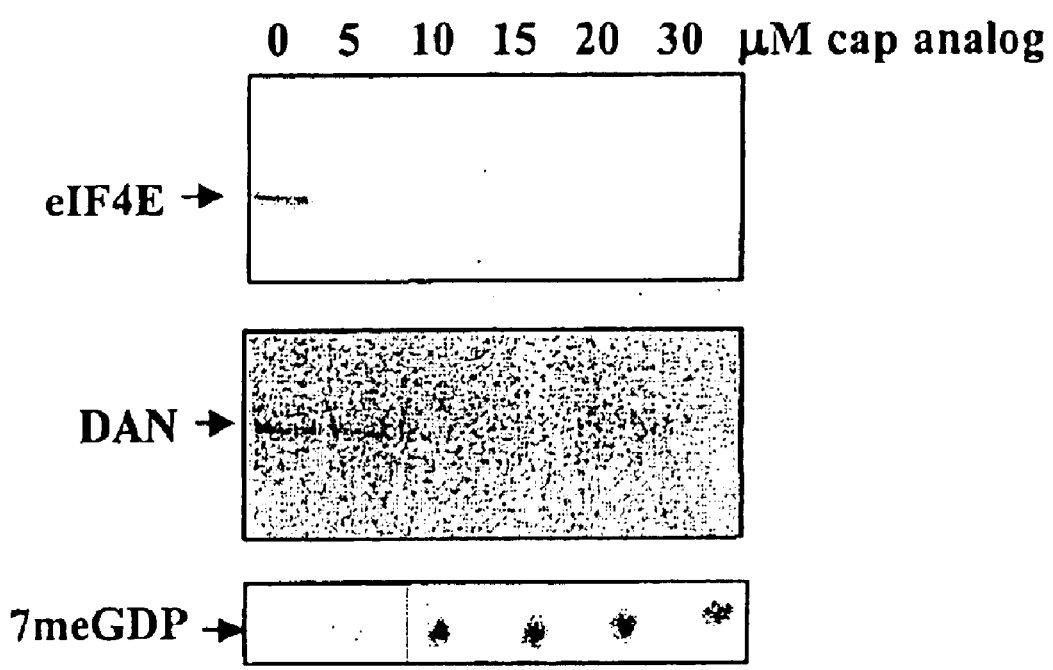
FIG. 2D. The indicated amounts of $^{7me}$GpppG or GpppG were incubated in HeLa S100 extracts using cap-labeled GemARE-A0 RNA under decapping conditions. The top panel shows UV cross-linking analysis or total protein as described in FIG. 2B to identify eIF4E. The middle panel shows UV cross-linking/immunoprecipitation analysis as described in FIG. 2C to identify DAN/PARN. The bottom panel shows the products of a decapping assay that were analyzed by thin layer chromatography as described in FIG. 2A.

In order to test the specificity of the activation of decapping in HeLa extracts by cap analog, the ability of methylated versus non-methylated cap analogs to activate decapping were compared. As seen in FIG. 2A, the presence of the methyl group on the cap analog was absolutely required to activate decapping. Decapping was activated by cap analog through the specific sequestration of cap-binding proteins. In order to confirm this, UV cross-linking assays were performed using cap labeled RNA substrates. As seen in FIG. 2B, the addition of increasing amounts of methylated cap analog to HeLa S100 extracts specifically competed for a 24 kDa protein. The 24 kDa protein is likely to be eIF4E (Altmann et al., 1985) since it has a similar apparent molecular weight, specifically cross-links to $^{7me}$cap structures, and is only detected in cytoplasmic extracts. Interestingly, Schwartz and Parker (2000) have recently demonstrated that purified yeast eIF4E can inhibit purified yeast decapping enzyme in vitro. Similar, but not identical amounts of $^{7me}$GpppG also specifically competed for cap binding by the deadenylase DAN/PARN (FIG. 2C). In order to determine whether the activation of decapping was correlated with the competition of the 24 kDa cap binding protein and/or DAN/PARN, careful titration experiments with cap analog were performed. As seen in FIG. 2D, decapping was only partially activated by the addition of 5 micromolar cap analog. This amount of cap analog fully sequestered the 24 kDa cap binding protein, but not DAN/PARN in the extracts. Full activation of decapping required 10micromolar cap analog, the amount required to fully sequester DAN/PARN. These data show that DAN/PARN may be a key factor in preventing decapping through interaction with the 5' cap. Specific removal of DAN/PARN from extracts by immunodepletion, however, failed to activate decapping. We conclude that a decapping activity with properties similar to the yeast Dcp1p enzyme exist in mammalian cytoplasmic extracts and can be specifically activated by sequestering cap binding activities. These data show that access to the cap structure is an important feature in the regulation of decapping in mammalian cells.

2. A Poly(A) Tail Represses Decapping of Mammalian mRNAs in a Poly(A) Binding Protein-Dependent Fashion Poly(A) tail shortening is a prerequisite for the decapping and turnover of most yeast mRNAs (Decker and Parker, 1993). This suggests that the presence of a poly(A) tail on RNA substrates represses decapping in vivo. In order to confirm that the in vitro decapping assay faithfully reproduces this regulatory aspect of in vivo decapping, matched RNA substrates were added to HeLa S100 extracts that either lacked a poly(A) tail (GemARE-A0, SVARE-A0 or GMCSFT-A0) or contained 60 adenylate residues at their 3' ends (GemARE-A60, SVARE-A60 or GMCSF-A60). The sizes of these transcripts vary from 95 to >700 bases to insure that results obtained were independent of the size of the transcript and could be generalized. As seen in FIG. 3, all 3 transcripts that lacked a poly(A) tail at their 3' end were efficiently decapped in S100 extract in the presence of cap analog. Their adenylated counterparts, however, were decapped at a dramatically reduced efficiency (10–20 fold). Note that the position of the $^{7me}$GDP spot varies depending on the time of incubation in the extract. In all cases, however, that radioactive spot co-migrates with $^{7me}$GDP as determined by UV shadowing of unlabeled markers that were loaded in each lane (altered migration is due to the generation of small molecules during the incubation of the extract that caused alteration in the chromatographic mobility of nucleotides on PEI cellulose). The presence of a poly(A) tail inhibits decapping in HeLa cytoplasmic extracts in a similar manner as has been observed in yeast (Muhlrad and Parker, 1994). The in vitro decapping assay reproduces this important regulatory aspect of mRNA turnover.

Figure 4A:
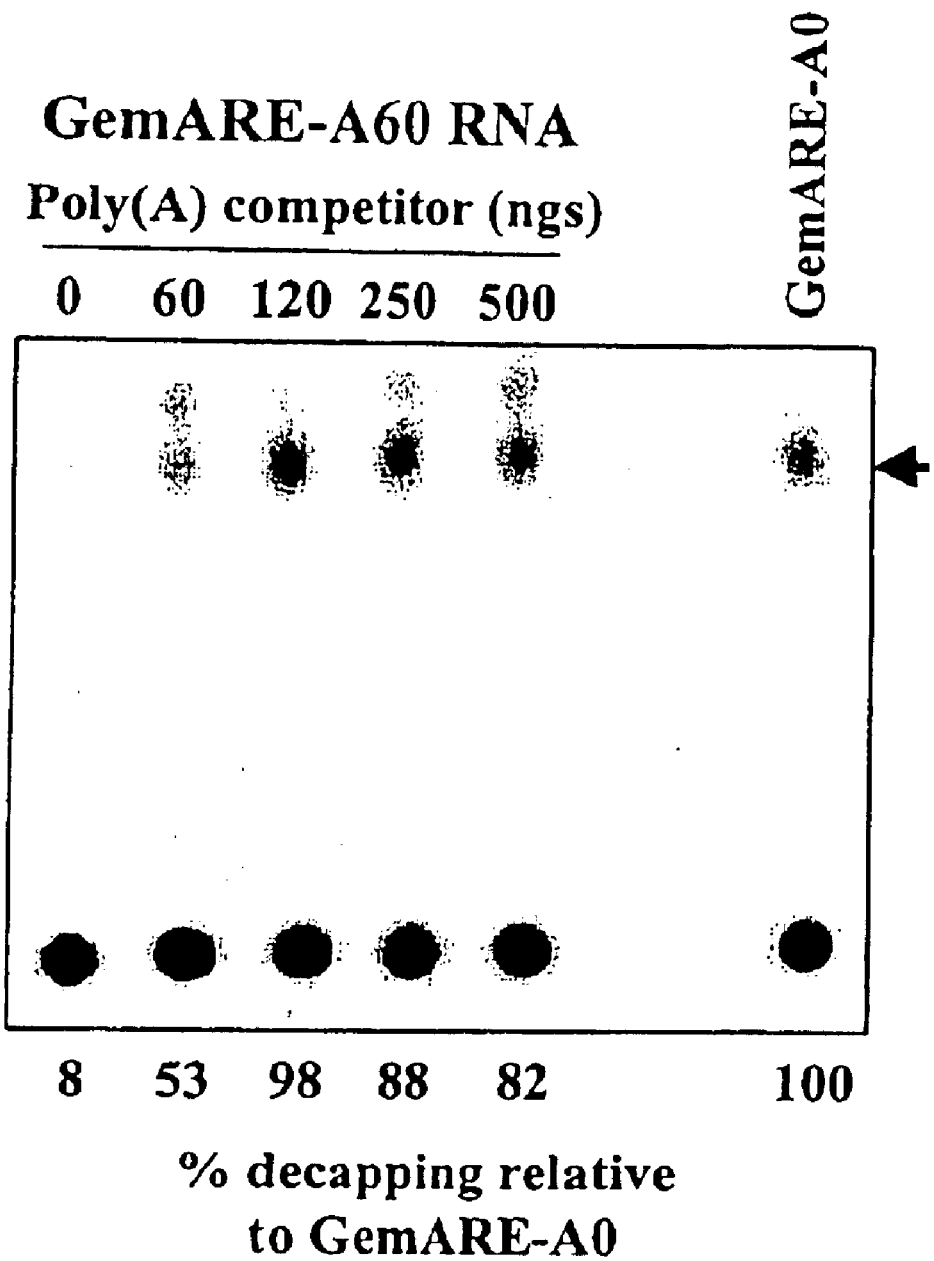
FIG. 4A. Cap-labeled GemARE-A60 RNA, which contained 60 adenylate residues at its 3' end, was incubated in the in vitro decapping system for 30 minutes in the presence of cap analog and the indicated amount of cold poly (A) competitor RNA. Reaction products were analyzed by thin layer chromatography on PEI cellulose sheets. In the lane marked GemARE-A0, GemARE-A0 RNA (that lacks a poly(A) tail) was incubated in the in vitro decapping assay in the absence of poly(A) RNA competitor.
Figure 4B:
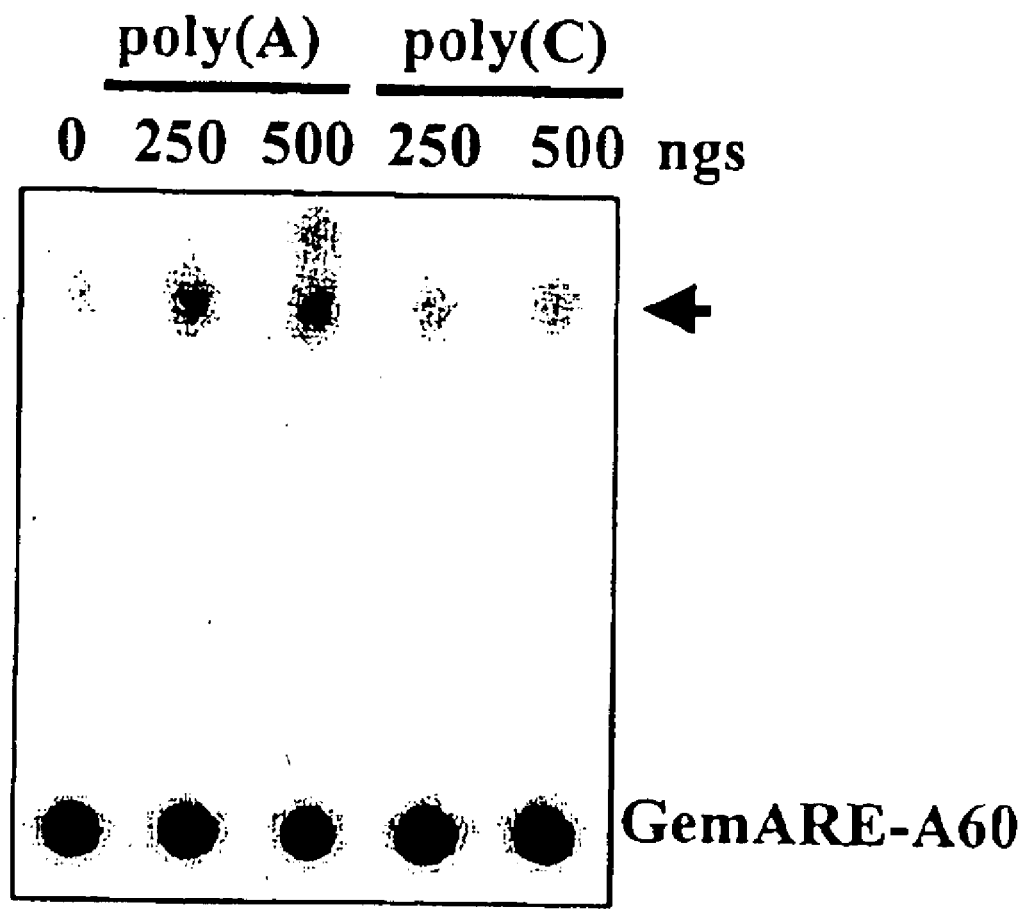
FIG. 4B Cap-labeled GemARE-A60 RNA, was incubated in the in vitro decapping system for 30 minutes in the presence of cap analog and the indicated amount of cold poly (A) or poly(C) competitor RNAs. Reaction products were analyzed by thin layer chromatography on PEI cellulose sheets. Input RNA was run in the lane designated input.
Figure 4C:
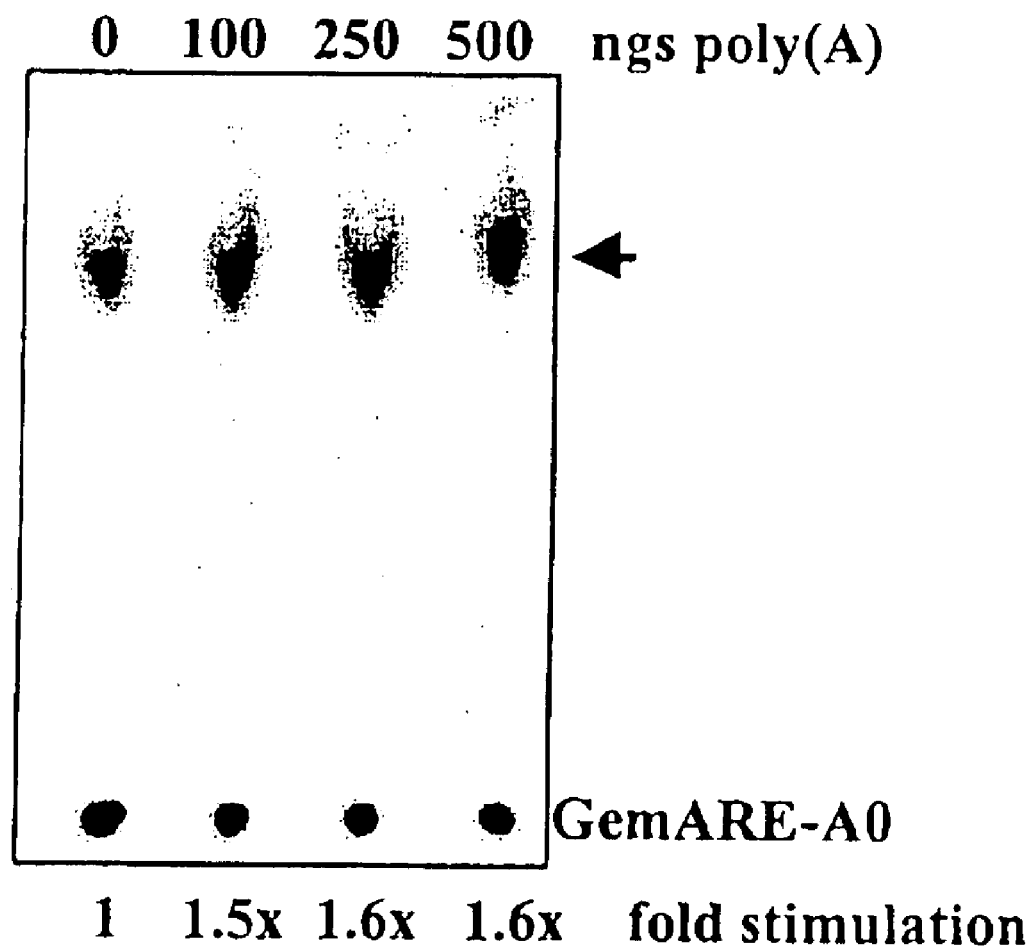
FIG. 4C. Cap-labeled GemARE-A0 RNA, which lacked a poly(A) tail, was incubated in the in vitro decapping system for 30 minutes in, the presence of cap analog and the indicated amount of cold poly(A) competitor RNA. Reaction products were analyzed by thin layer chromatography on PEI cellulose sheets. For all three FIGS. 4A, 4B and 4C, the position of $^{7me}$GDP is indicated by the arrowhead.

In order to assess the involvement of poly(A) binding proteins in the mechanism of poly(A) tail-mediated repression of decapping, increasing amounts of poly(A) competitor RNA were added to in vitro decapping assays using an RNA substrate that possessed a 60 base poly(A) tail. As seen in FIG. 4A, the addition of cold poly(A) competitor RNA that inhibited the cross-linking of a 70 kDA poly(A) binding protein to the poly(A) tail (Ford and Wilusz, 1999, data not shown) effectively stimulated decapping to levels observed with deadenylated substrates. Similar data were obtained for all RNA substrates tested. Since the decapping assays are performed in the presence of cap analog that sequesters the deadenylase DAN/PARN, deadenylation of the RNA substrate is not occurring under these conditions (Gao et al., 2000) and, therefore, cannot account for the results obtained. Furthermore, poly(A) competitor RNA failed to stimulate decapping in the absence of cap analog. The presence of free cap-binding proteins in extracts is a dominant inhibitor to in vitro decapping. The stimulation of decapping was specific for poly(A), as other homopolymers such as poly(C) did not appreciably affect decapping of all RNA substrates tested (FIG. 4B). Finally, we tested whether the stimulation of decapping by poly(A) competitor RNA was a general activator of decapping or was specific for adenylated transcripts. As seen in FIG. 4C, the decapping of an RNA substrate that lacked a poly(A) tail (GemARE-A0) was only mildly stimulated by the addition of poly(A) competitor RNA. The small (1.5-fold) effect of poly(A) on decapping of the GemARE-A0 RNA substrate is likely due to the low affinity of poly(A) binding protein for the AU-rich element contained in the 3' portion of the transcript (D. Fritz and J. Wilusz, data not shown). Similar data was also obtained for all RNA substrates tested that lacked a 3' poly(A) tail . Poly(A) binding proteins are repressors of decapping when bound to poly (A)$^+$ RNA substrates. Furthermore, since the decapping assays are performed in the presence of $^{7me}$GpppG that sequesters eIF4E (FIG. 2), the repression of decapping by poly(A) binding proteins occurs in a novel, eIF4E-independent fashion.

3. AU-Rich Instability Elements Dramatically Stimulate Decapping

Figure 5C:
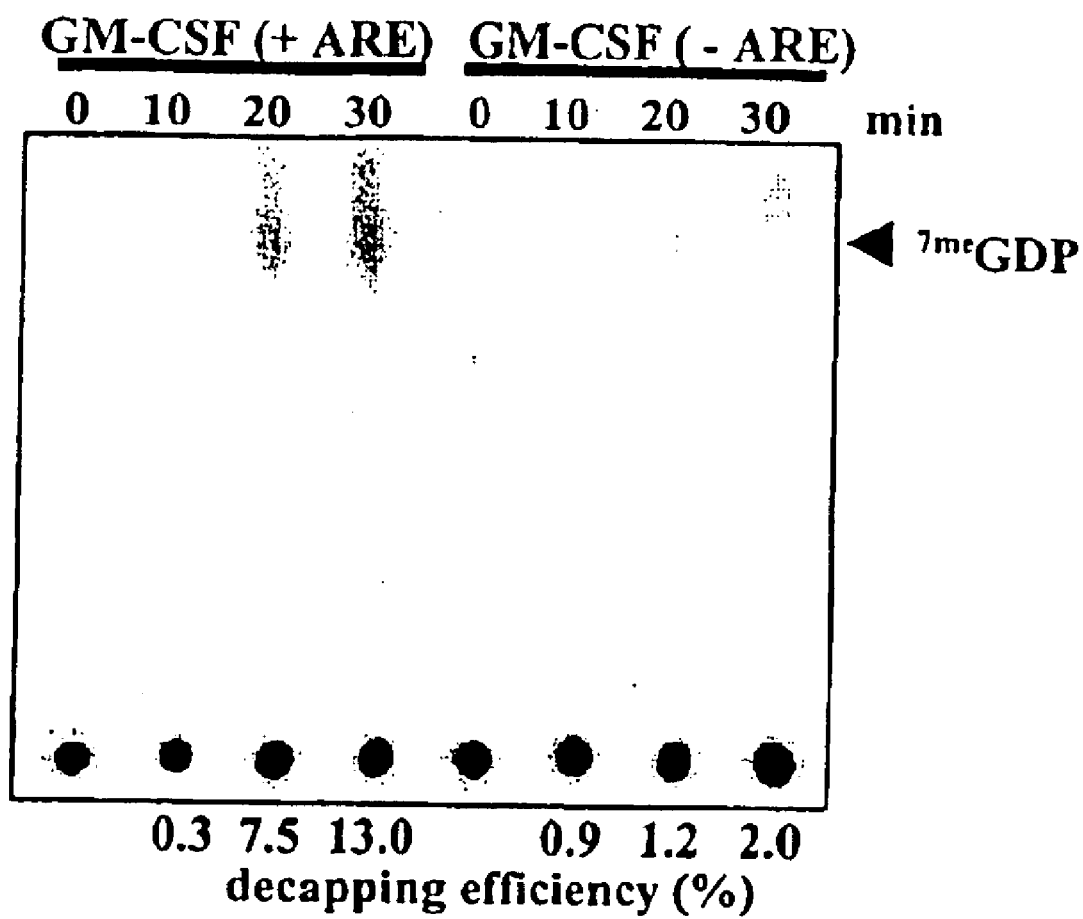
FIG. 5C. A matched pair of cap-labeled RNA substrates that either lacked (GM-CSF(-ARE)) or contained the GM-CSF AU-rich element (G-CSF(+ARE)) were incubated in the in vitro decapping system in the presence of cap analog for the indicated amount of time. Reaction products were analyzed by thin layer chromatography on PEI cellulose sheets. For all three FIGS. 5A, 5B and 5C, the position of $^{7me}$GDP is indicated by an arrowhead.

Many short-lived mammalian mRNAs contain AU-rich elements in their 3' untranslated regions that have been shown to be directly responsible for the high rate of turnover of these transcripts (Chen and Shyu, 1995). While AU-rich instability elements have been shown to increase the rate of deadenylation both in vivo (Shaw and Kamen, 1986; Shyu et al., 1989) and in vitro (Ford et al., 1999), efficient deadenylation requires an interaction between DAN/PARN and the 5' cap structure (Gao et al., 2000). AU-rich elements are be capable of stimulating deadenylation by making the cap structure more accessible to the deadenylase, and AU-rich elements are also be able to stimulate decapping by a similar mechanism. Two independent RNA substrates either lacked (Gem-A0 and SV-A0) or contained (GemARE-A0 and SVARE-A0) the AU-rich element from the TNF-alpha mRNA. As seen in FIGS. 5A and B, the presence of the TNF-alpha AU-rich element in an RNA substrate stimulated decapping over 10-fold. In order to generalize this observation to other AU-rich elements, an RNA that contained the GM-CSF ARE or a matched control transcript that lacked the element was prepared. As seen in FIG. 5C, the AU-rich element from the GM-CSF mRNA also strongly stimulated decapping in vitro. We conclude that AU-rich instability elements dramatically stimulate decapping.

Figure 6:
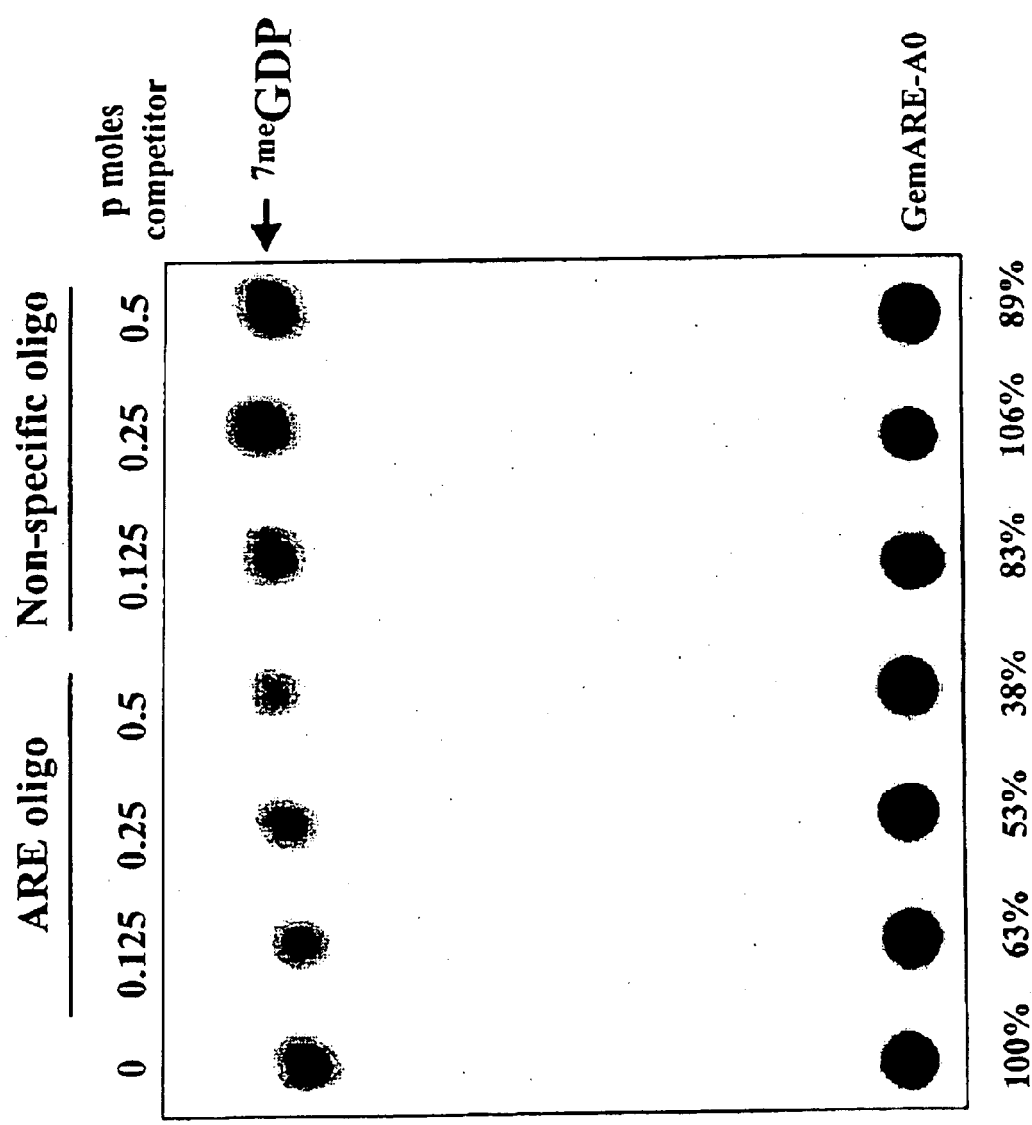
FIG. 6. The stimulation of decapping by AU-rich elements requires sequence-specific AU-rich element binding factors. Cap-labeled GemARE-A0 RNA (Panel A) or Gem-A0 RNA (Panel B) was incubated in the in vitro decapping system in the presence of cap analog and the indicated amount of a 34 base synthetic RNA competitor derived from the TNF-alpha AU-rich element (ARE oligo lanes) or a 33 mer derived from randomly selected sequences (non-specific oligo lanes). Reaction products were analyzed by thin layer chromatography on PEI cellulose sheets. The position of $^{7me}$GDP is indicated by an arrowhead. The numbers at the bottom refer to decapping efficiency relative to lane 0.
Figure 7:
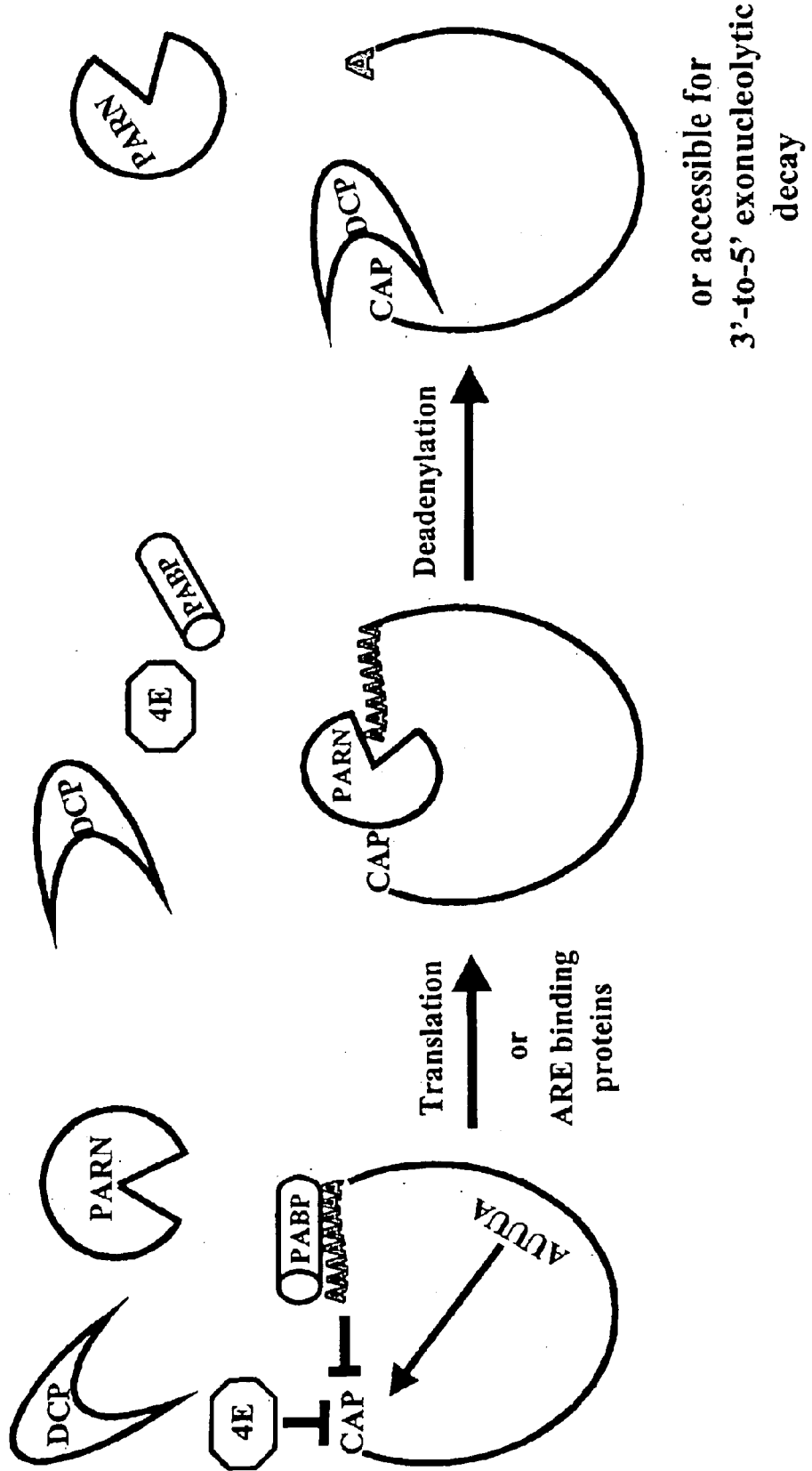
FIG. 7: A model for the regulated mRNA decapping. The mRNA cap structure is normally stabilized by interactions with eIF4E and/or a novel PABP complex. The process of translation or the action of AU-rich element binding proteins can disrupt these complexes involving the 5' cap, exposing the ends of the transcript to the deadenylation machinery. Following poly(A) tail shortening, the affinity of DAN/PARN for the mRNA is dramatically reduced, allowing the decapping enzyme (as well as other degradative enzymes such as 3'-to-5' exonucleases) access to the ends of the mRNA.
Figure 8A:
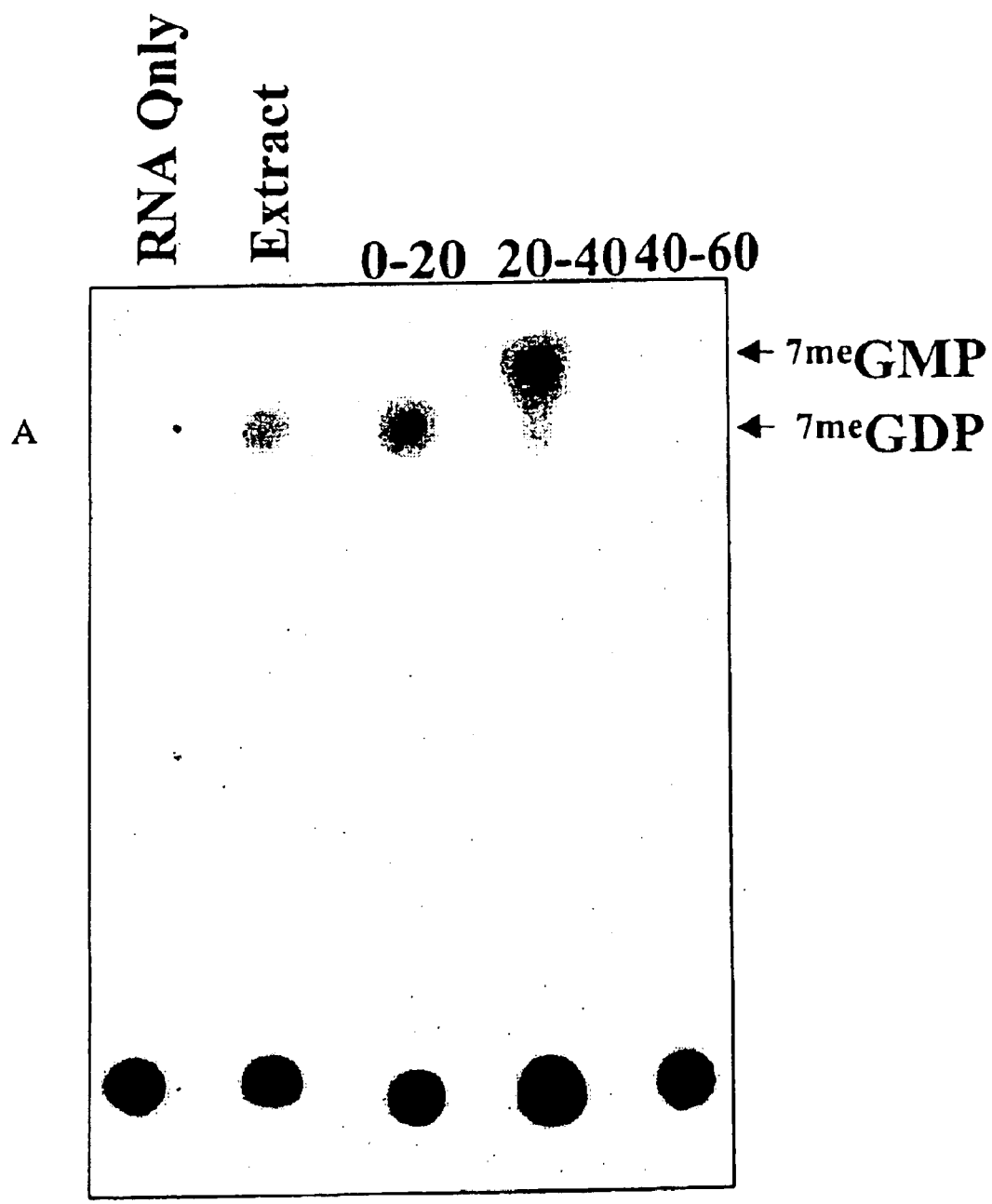
FIG. 8A. Ammonium sulfate fractionation of decapping activity in Hela FIG 8B. Chromatographic profile of decapping activity on a Superose-6 column.
Figure 8B:
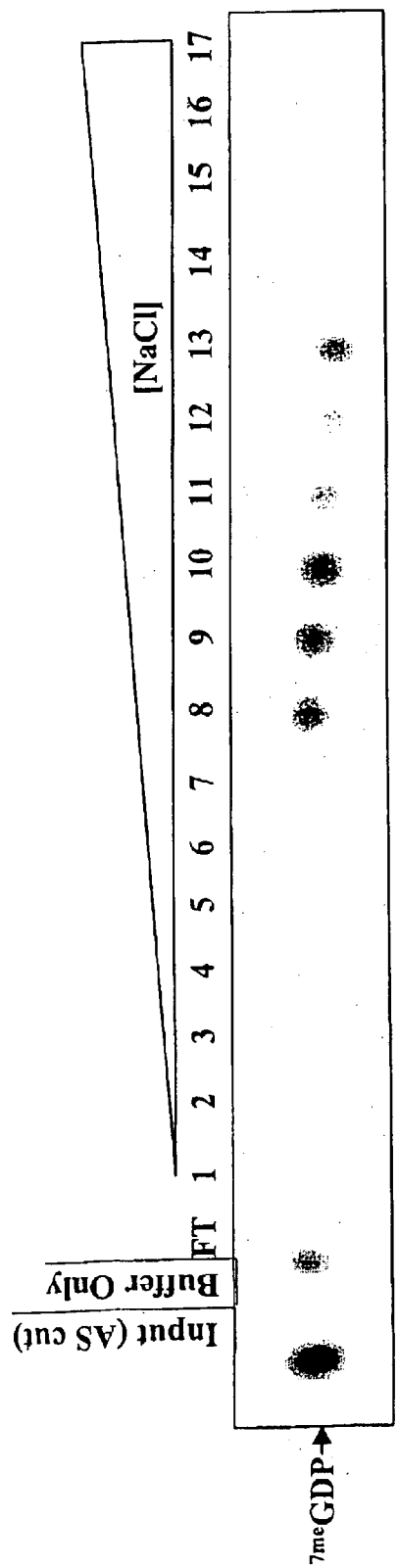
FIG. 8: Partial purification of decapping activity from Hela cytoplasmic extract.
FIG. 8C. Chromatographic profile of decapping activity on a Heparin-Sepharose column.
Figure 8C:
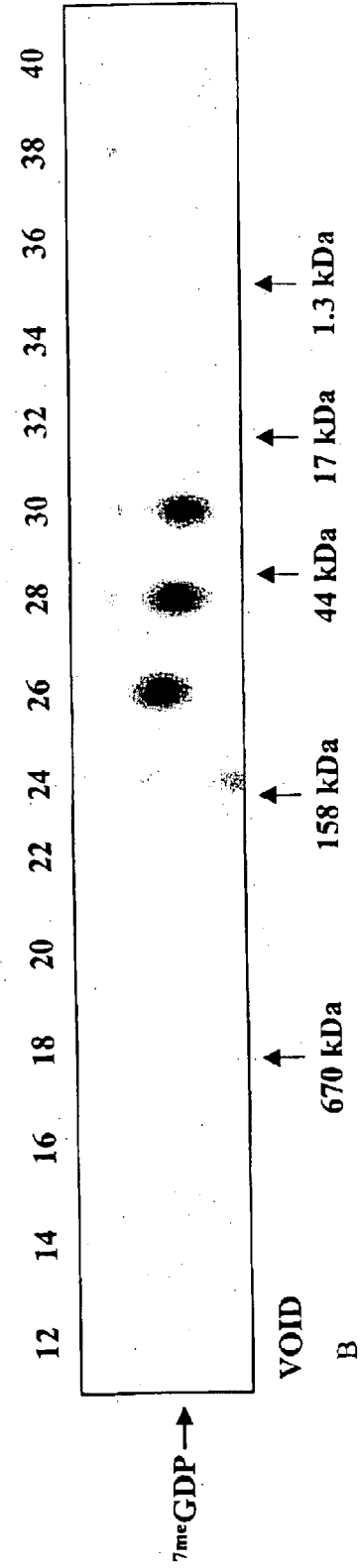

The AU-rich element binding proteins (ARE-BPs) play a role in the stimulation of decapping by the instability element. In order to sequester ARE-BPs in S100 extracts, increasing amounts of a 34 base synthetic RNA oligomer containing the TNF-alpha AU-rich element (ARE) were added to in vitro decapping assays. In control reactions, similar amounts of an unrelated 33 base RNA were added. As seen in FIG. 6, the addition of the ARE competitor RNA significantly reduced decapping of an AU-rich element-containing RNA substrate while similar levels of the control competitor RNA had no effect on decapping efficiency. The reduction in decapping efficiency by the ARE synthetic RNA competitor was only observed with RNA substrates that contained an AU-rich element (FIG. 6B). Finally, UV cross-linking assays correlated the competition of a specific ARE-binding protein by the ARE competitor RNA with repression of decapping. Both ARE-specific RNA binding proteins that we observed in our UV cross-linking assays, HuR (a known mRNA stabilizer) and an unidentified 40 kDa species (Ford et al., 1999), were competed by the ARE RNA oligomer with exactly the same concentration dependence and kinetics.

4. Identification and Purification of Human Decapping Protein

The decapping protein (preferably an enzyme) from Hela cells purified sing a combination of conventional and affinity chromatography steps. The majority of Hela decapping activity can be precipitated by 20% ammonium sulfate. Molecular exclusion chromatography using a Sepharose-6 column indicates that the decappin activity elutes in the ~50~100 kDa range, consistent with a single (or few) polypeptides being responsible for enzymatic activity. Therefore following decapping activity through purification will likely not require reconstitution of multiple fractions as would be the case with large multi-component complexes (i.e. 20). The bulk of decapping activity elutes between 440 and 550 mM NaCl from a heparin-sepharose column (See FIG. 8, FIGS. 8A, 8B, 8C).

a. Fractionation i. Starting material: S100 cytoplasmic extract from HeLa spinner cells is prepared in bulk by known methods and as described herein (see, for example, Ford, et al, 1999 and Ford and Wilusz, 1999).

ii. Assays for factors during fractionation: As the purification proceeds, decapping activity is followed through sequential purification steps using the In vitro Decapping Assay described above in section A.3. This assay is easy to perform, gives rapid and quantitative results, and is highly reproducible. Since the yeast decapping enzyme is contained in a single polypeptide, individual fractions are first tested to identify HeLa decapping activity, and appropriate fractions mixed/matched if necessary to reconstitute active decapping. Fraction purity is assessed by silver staining of fractions run on SDS-PAGE gels using known methods.

iii.Purification:. Extracts are initially fractionated by an ammonium sulfate cut of 20% saturation. All of the decapping activity is precipitated at these levels of saturation. A range of conventional and well known fractionation methods on an analytical scale may be used for optimal purification protocols. At each step, fractions are assayed using the decapping assay in order to confirm that the decapping protein (or enzyme) is present in the fraction.

The available methods include anion exchange columns (DEAE), phosphocellulose, cation exchange columns (S-sepharose, heparin), molecular exclusion (Superose 6), hydrophobic interactions columns (phenyl-sepharose) and step elutions to identify optimal purification steps. Affinity columns such as dye ligand chromatography and nucleic acid columns are also available. Linear elution gradients are employed to optimize purification efficiencies. As purification continues, fractions may be mixed and matched as required to reconstitute activity.

Successful analytical steps may be increased to preparative scale using available high resolution columns (Amersham-Pharmacia). Buffer exchanges will be performed using conventional dialysis or Centricon columns where applicable. An automated Amersham-Pharmacia AKTA purification system, UV monitor and fraction collector may used for these efforts. All purifications are preferably performed at 4 degrees C. in the presence of protease inhibitors (PMSF, leupeptin and others, if necessary).

Fractions should be kept as concentrated as possible, and glycerol and DTT should be present in all buffers, and NP40 or carrier proteins may be added to further maintain stability if necessary. Fractions are best maintained if quick frozen in liquid nitrogen and stored at–80 degrees C.

b. Molecular Characterization of the Mammalian Decapping Protein i. Peptide sequencing: Following purification to near homogeneity, proteins that co-fractionate with decapping activity are excised from denaturing gels and subjected to mass spectrophotometiy and/or micro-sequencing by known methods. Since many peptide sequences are now known, MALDI-MS should be performed on samples as a first step followed by database searches using Peptide Search I software.

ii. cDNA clones: Identified cDNA clones may be obtained by many techniques, most conveniently by RT-PCR amplification using appropriate primers based on the above sequence analysis. Alternatively, library screening can be performed by conventional methods using frozen HeLa cDNA libraries using appropriate probes based on the above sequence analysis.

iii. Full-length clones: Full-length clones of the decapping activity are obtained as described above and may be sequenced and analyzed for interesting motifs that will yield insights into its structure/function and/or regulation. Such motifs include enzymatic signatures, RNA binding domains, phosphorylation sites, etc. Full-length ORFs are cloned into bacterial expression vectors (such as pGEX and/or pRSET) and induced to express high levels of recombinant decapping protein(s). Alternatively, yeast or baculovirus expression systems can be used if proteins made in bacteria are difficult to express or are inactive. Proteins will be purified using Ni or glutathione affinity columns and tested for decapping activity in vitro with cap-labeled RNA substrates to confirm the identity of the decapping enzyme. Alternatively, HeLa cell proteins eluted from denaturing gels can be renatured (100) to identify enzymatic subunits.

iv. Antibodies: Antibodies may be generated using conventional methods from the isolated and purified peptide(s) having decapping activity. These immunologic reagents will be very useful in assessing (A) the subcellular localization (an especially interesting question given the nuclear association of some aspects of nonsense-mediated decay process that may be regulated through decapping); (B) developmental and tissue-specific expression patterns; (C) assessing post-translational modifications of decapping proteins; (D) depletion/add back studies; and (E) as an invaluable reagent for future protein-protein interaction studies to identify factors that associate with the decapping enzyme and may regulate its activity. Both monoclonal and polyclonal antibodies are contemplated.

5. Effect of Pyrimidine-rich Stability Element on Decapping Rates

The alpha-globin element was inserted into three independent RNA substrates and in vitro decapping rates were assessed in HeLa extracts using the decapping assay outlined above. RNAs that contained the alpha-globin element showed at least a 2-fold and up to a 10 fold decrease in decapping efficiency compared to control RNAs (FIG. 9). Furthermore, the alpha-globin element also repressed decapping of RNA substrates that contained an AU-rich instability element, showing that the alpha-globin element exerted a dominant influence over the AU-rich instability element. In order to evaluate whether proteins play a role in the repression of decapping by the alpha-globin element, competition assays were performed. The addition of unlabeled competitor RNAs that contained the alpha-globin element specifically restored decapping efficiency to wild-type rates. In summary, these data demonstrate that proteins that bind to the alpha-globin element can stabilize mRNAs through a novel mechanism, either by regulating accessibility of the cap or interacting directly with factors involved in decapping.

Isolation of protein factors that repress decapping using the standard approaches to identify RNA binding proteins (i.e. UV crosslinking, mobility shifts in combination with conventional affinity chromatography, northwestern screening, three hybrid assays, etc., is contemplated, as well as isolation of the polynucleotides encoding this protein, and antibodies to this protein, also as described above.

REFERENCES

Allmang, C., Petfalski, E., Podtelejnikov, A., Mann, M., Tollervey, D., and Mitchell, P. (1999) The yeast exosome and human PM-Scl are related complexes of 3'→5' exonucleases. *Genes Dev.* 13, 2148–2158.

Altmann, M., Edery, I., Sonenberg, N., and Trachsel, H. (1985) Purification and characterization of protein synthesis initiation factor eIF-4E from the yeast *Saccharomyces cerevisiae*. *Biochemistry* 24, 6085–6089.

Beelman, C. A., Stevens, A., Caponigro, G., LaGrandeur, T. E., Hatfield, L., Fortner, D. M., and Parker, R. (1996) An essential component of the decapping enzyme required for normal rates of mRNA turnover. *Nature* 382, 642–646.

Bonnerot, C., Boeck, R., and Lapeyre, B. (2000) The two proteins pat1p (Mrt1p) and spb8p interact in vivo, are required for mRNA decay, and are functionally linked to pab1p. *Mol. Cell. Biol.* 20, 5939–5946.

Bousquet-Antonelli, C., Presutti, C. and Tollervey, D. (2000) Identification of a regulated pathway for nuclear pre-mRNA turnover. *Cell* 102, 765–775.

Bouveret, E., Rigaut, G., Shevchenko, A., Wilm, M., and Seraphin, B. (2000) A Sm-like protein complex that participates in mRNA degradation. *EMBO J.* 19, 1661–1671.

Brewer, G. (1991) An A+U-rich element RNA-binding factor regulates c-myc mRNA stability in vitro. *Mol. Cell. Biol.* 11, 2460–2466.

Caponigro, G., and Parker, R. (1996) Mechanisms and control of mRNA turnover in *Saccharomyces cerevisiae*. *Microbiol Rev.* 60, 233–249.

Caponigro, G., and Parker, R. (1995) Multiple functions for the poly(A)-binding protein in mRNA decapping and deadenylation in yeast. *Genes Dev.* 9, 2421–2432.

Chen, C. Y., and Shyu, A. B. (1995) AU-rich elements: characterization and importance in mRNA degradation. *Trends Biochem. Sci.* 20,465–470.

Couttet, P., Fromont-Racine, M., Steel, D., Pictet, R., and Grange, T. (1997) Messenger RNA deadenylylation precedes decapping in mammalian cells. *Proc. Natl. Acad. Sci. USA* 94,5628–5633.

Czaplinski, K., Ruiz-Echevarria, M. J., Gonzalez, C. I., and Peltz, S. W. (1999) Should we kill the messenger? The role of the surveillance complex in translation termination and mRNA turnover. *Bioessays* 21, 685–696.

Decker, C. J., and Parker, R. (1993) A turnover pathway for both stable and unstable mRNAs in yeast: evidence for a requirement for deadenylation. *Genes Dev.* 7, 1632–1643.

Dehlin, E., Wormington, M., Korner, C. G., and Wahle, E. (2000) Cap-dependent deadenylation of mRNA. *EMBO J.* 19, 1079–1086.

Dunckley, T., and Parker, R. (1999) The DCP2 protein is required for mRNA decapping in *Saccharomyces cerevisiae* and contains a functional MutT motif. *EMBO J.* 18, 5411–5422.

Fan, X. C., and Steitz, J. A. (1998) Overexpression of HuR, a nuclear-cytoplasmic shuttling protein, increases the in vivo stability of ARE-containing mRNAs. *EMBO J.* 17, 3448–3460.

Ford, L. P., Bagga, P. S., and Wilusz, J. (1997) The poly(A) tail inhibits the assembly of a 3'-to-5' exonuclease in an in vitro RNA stability system. *Mol. Cell. Biol.* 17, 398–406.

Ford, L. P., Watson, J., Keene, J. D., and Wilusz, J. (1999) ELAV proteins stabilize deadenylated intermediates in a novel in vitro mRNA deadenylation/degradation system. *Genes Dev.* 13, 188–201.

Ford, L. P., and Wilusz, J. (1999) An in vitro system using HeLa cytoplasmic extracts that reproduces regulated mRNA stability. *Methods* 17, 21–27.

Gao, M., Fritz, D. T., Ford, L. P., and Wilusz, J. (2000) Interaction between a poly(A)-specific ribonuclease and the 5' cap influences mRNA deadenylationrates in vitro. *Mol. Cell* 5,479–488.

Gray, N. K., Coller, J. M., Dickson, K. S. and Wickens, M. (2000) Multiple portions of poly(A)-binding protein stimulate translation in vivo. *EMBO J.* 19, 4723–4733.

Hagan, K. W., Ruiz-Echevarria, M. J., Quan, Y., and Peltz, S. W. (1995) Characterization of cis-acting sequences and decay intermediates involved in nonsense-mediated mRNA turnover. *Mol. Cell. Biol.* 15, 809–823.

Hsu, C. L., and Stevens, A. (1993) Yeast cells lacking 5'→3' exoribonuclease 1 contain mRNA species that are poly(A) deficient and partially lack the 5' cap structure. *Mol. Cell. Biol.* 13, 4826–4835.

Imataka, H., Gradi, A., and Sonenberg, N. (1998) A newly identified N-terminal amino acid sequence of human eIF4G binds poly(A)-binding protein and functions in poly(A)-dependent translation. *EMBO J.* 17, 7480–7489.

Jacobs Anderson, J. S. and Parker, R. (1998) The 3' to 5' degradation of yeast mRNAs is a general mechanism for mRNA turnover that requires the SKI2 DEVH box protein and 3' to 5' exonucleases of the exosome complex. *EMBO J.* 17, 1497–1506.

Jacobson, A., and Peltz, S. W. (1996) Interrelationships of the pathways of mRNA decay and translation in eukaryotic cells. *Annu. Rev. Biochem.* 65, 693–739.

Korner, C. G., Wormington, M., Muckenthaler, M., Schneider, S., Dehlin, E., and Wahle, E. (1998) The deadenylating nuclease (DAN) is involved in poly(A) tail removal during the meiotic maturation of *Xenopus* oocytes. *EMBO J.* 17, 5427–5437.

LaGrandeur, T. E., and Parker, R. (1998) Isolation and characterization of Dcp1p, the yeast mRNA decapping enzyme. *EMBO J.* 17,1487–1496.

Lai, W. S., Carballo, E., Strum, J. R., Kennington, E. A., Phillips, R. S., and Blackshear, P. J. (1999) Evidence that tristetraprolin binds to AU-rich elements and promotes the deadenylation and destabilization of tumor necrosis factor alpha mRNA. *Mol. Cell. Biol.* 19, 4311–4323.

Levine, T. D., Gao, F., King, P. H., Andrews, L. G., and Keene, J. D. (1993) Hel-N1: an autoimmune RNA-binding protein with specificity for 3' uridylate-rich untranslated regions of growth factor mRNAs. *Mol. Cell. Biol.* 13, 3494–3504.

Lin, R. J., Newman, A. J., Cheng, S. C., and Abelson, J. (1985) Yeast mRNA splicing in vitro. *J. Biol. Chem.* 260,14780–14792.

Loflin, P., Chen, C. Y., and Shyu, A. B. (1999) Unraveling a cytoplasmic role for hnRNP D in the in vivo mRNA destabilization directed by the AU-rich element. *Genes Dev.* 13, 1884–1897.

Losson, R., and Lacroute, F. (1979) Interference of nonsense mutations with eukaryotic messenger RNA stability. *Proc. Natl. Acad. Sci. USA* 76, 5134–5137.

Ma, W. J., Cheng, S., Campbell, C., Wright, A., and Fumeaux, H. (1996) Cloning and characterization of HuR, a ubiquitously expressed Elav-like protein. *J. Biol. Chem.* 271, 8144–8151.

Mitchell, P., and Tollervey, D. (2000) mRNA stability in eukaryotes. *Curr. Opin. Genet. Dev.* 10, 193–198.

Morrissey, J. P., Deardorff, J. A., Hebron, C., and Sachs, A. B. (1999) Decapping of stabilized, polyadenylated mRNA in yeast pab1 mutants. *Yeast* 15, 687–702.

Muhlrad, D., Decker, C. J., and Parker, R. (1994) Deadenylation of the unstable mRNA encoded by the yeast MFA2 gene leads to decapping followed by 5'→3' digestion of the transcript. *Genes Dev.* 8, 855–866.

Muhlrad, D., and Parker, R. (1994) Premature translational termination triggers mRNA decapping. *Nature* 370, 578–581.

Nuss, D. L., Furuichi, Y., Koch, G., and Shatkin, A. J. (1975) Detection in HeLa cell extracts of a 7-methyl guanosine specific enzyme activity that cleaves m7GpppNm. *Cell* 6, 21–27.

Peng, S. S., Chen, C. Y., Xu, N., and Shyu, A. B. (1998) RNA stabilization by the AU-rich element binding protein, HuR, an ELAV protein. *EMBO J.* 17, 3461–3470.

Sachs, A. B., and Varani, G. (2000) Eukaryotic translation initiation: there are (at least) two sides to every story. *Nat. Struct. Biol.* 7, 356–361.

Schwartz, D. C., and Parker, R. (1999) Mutations in translation initiation factors lead to increased rates of deadenylation and decapping of mRNAs in *Saccharomyces cerevisiae*. *Mol. Cell. Biol.* 19, 5247–5256.

Schwartz, D. C. and Parker, R. (2000) mRNA decapping in yeast requires dissociatiion of the cap binding protein, eukaryotic translation initiation factor 4E. *Mol. Cell. Biol.* 20, 7933–7942.

Shaw, G., and Kamen, R. (1986) A conserved AU sequence from the 3' untranslated region of GM-CSF mRNA mediates selective mRNA degradation. *Cell* 46, 659–667.

Shyu, A. B., Belasco, J. G., and Greenberg, M. E. (1991) Two distinct destabilizing elements in the c-fos message trigger deadenylation as a first step in rapid mRNA decay. *Genes Dev.* 5, 221–231.

Shyu, A. B., Greenberg, M. E., and Belasco, J. G. (1989) The c-fos transcript is targeted for rapid decay by two distinct mRNA degradation pathways. *Genes Dev.* 3, 60–72.

Sonenberg, N., and Gingras, A. C. (1998) The mRNA 5' cap-binding protein eIF4E and control of cell growth. *Curr. Opin. Cell. Biol.* 10: 268–275.

Sonenberg, N., Morgan, M. A., Merrick, W. C., and Shatkin, A. J. (1978) A polypeptide in eukaryotic initiation factors that crosslinks specifically to the 5'-terminal cap in mRNA. *Proc. Natl. Acad. Sci. USA* 75, 4843–4847.

Tharun, S., He, W., Mayes, A. E., Lennertz, P., Beggs, J. D., and Parker, R. (2000) Yeast Sm-like proteins function in mRNA decapping and decay. *Nature* 404, 515–518.

Tucker, M and Parker, R. (2000) Mechanisms and control of mRNA decapping in *saccharomyces cerevisiae*. *Annu. Rev. Biochem.* 69, 571–595.

Vilela, C., Velasco, C., Ptushkina, M., and McCarthy, J. E. (2000) The eukaryotic mRNA decapping protein Dcp1 interacts physically and functionally with the eIF4F translation initiation complex. *EMBO J.* 19, 4372–4382.

Wang, Z., Day, N., Trifillis, P., and Kiledjian, M. (1999) An mRNA stability complex functions with poly(A)-binding protein to stabilize mRNA in vitro. *Mol. Cell. Biol.* 19, 4552–4560.

Wells, S. E., Hillner, P. E., Vale, R. D., and Sachs, A. B. (1998) Circularization of mRNA by eukaryotic translation initiation factors. *Mol Cell* 2, 135–140.

Wilson, T., and Treisman, R. (1988) Removal of poly(A) and consequent degradation of c-fos mRNA facilitated by 3' AU-rich sequences. *Nature* 336, 396–399.

Wilusz, J., and Shenk, T. (1988) A 64 kd nuclear protein binds to RNA segments that include the AAUAAA polyadenylation motif. *Cell* 52,221–228.

Zhang, S., Williams, C. J., Hagan, K., and Peltz, S. W. (1999a) Mutations in VPS16 and MRT1 stabilize mRNAs by activating an inhibitor of the decapping enzyme. *Mol. Cell. Biol.* 19,7568–20 7576.

Zhang, S., Williams, C. J., Wormington, M., Stevens, A., and Peltz, S. W. (1999b) Monitoring mRNA decapping activity. *Methods* 17,46–51.

Zuk, D., Belk, J. P. and Jacobson, A. (1999) Temperature sensitive mutants in the *saccharomyces cerevisiae* MRT4, GRC5, SLA2 and THS1 genes result in defects in mRNA turnover. *Genetics* 153, 35–47.

What is claimed is:

1. A mammalian in vitro mRNA decapping system comprising:
   a) polysome-free HeLa cell cytoplasmic extract;
   b) a methylated cap analog and
   c) a cap-labeled mRNA substrate.

2. The mammalian in vitro mRNA decapping system of claim 1 wherein said methylated cap analog is $^{7me}$GpppG or $^{7me}$GTP.

3. The mammalian in vitro mRNA decapping system of claim 1 wherein said cap-labeled mRNA substrate is labeled at the alpha phosphate of the cap.

4. The mammalian in vitro mRNA decapping system of claim 1 wherein said cap-labeled mRNA substrate is labeled at the cap of said cap-lableed mRNA substrate by a label selected from the group consisting of a radioactive label, a non-radioactive isotopic label, a fluorescent moiety, a visibly-detectable moiety, releasable substrate, a co-factor for a chemical reaction, and a co-factor for a enzymatic reaction.

5. The mammalian in vitro mRNA decapping system of claim 1 further comprising means for sequestering proteins that bind to poly(A).

6. The mammalian in vitro mRNA decapping system of claim 1 wherein said HeLa cell cytoplasmic extract is a HeLa S100 cell cytoplasmic extract.

7. The mammalian in vitro mRNA decapping system of claim 6 wherein said HeLa cell cytoplasmic extract is prepared by dialysis of said extract containing 10% glycerol.

8. The mammalian in vitro mRNA decapping system of claim 6 wherein said S100 cell cytoplasmic extract comprises a 100,000×g, 1 hour supernatant from a HeLa cell lysate.

9. The mammalian in vitro mRNA decapping system of claim 1 wherein said cap-labeled mRNA substrate comprises poly(A) or at lea one RNA element.

10. The manunalian in vitro mRNA decapping system of claim 9 wherein said RNA element is a pyrimidine-rich element.

11. The mammalian in vitro mRNA decapping system of claim 9 further comprising means for stimulating decapping of the cap-labeled mRNA substrate wherein the cap-labeled mRNA substrate comprises poly(A).

12. The mammalian in vitro mRNA decapping syst of claim 9 further comprising a cold poly(A) competitor RNA.

13. The mammalian in vitro mRNA decapping system of claim 9 wherein said RNA element is an AU-rich element.

14. The mammalian in vitro mRNA decapping system of claim 13 further comprising means for reducing decapping of the cap-labeled mRNA substrate.

15. The mammalian in vitro mRNA decapping system of claim 13 further comprising an AU-rich element competitor RNA.

16. A kit for measuring mRNA decapping in vitro comprising:
   a) a polysome-free HeLa cell cytoplasmic extract;
   b) a methylated cap analog; and
   c) cap-labeled mRNA substrate.

17. The kit of claim 16 wherein said cap-labeled mRNA substrate is labeled at the alpha phosphate of the cap.

18. The kit of claim 16 wherein said cap-labeled mRNA substrate is labeled at the cap of said cap-labeled mRNA substrate by a label selected from the group consisting of a radioactive label, a non-radioactive isotopic label, a fluorescent moiety, a visibly-detectable moiety, a releasable substrate, a co-factor for a chemical reaction, and a co-factor for an enzymatic reaction.

19. The kit of claim 16 wherein the polysome-free HeLa cell cytoplasmic extract is HeLa S100 cell cytoplasmic extract.

20. The kit of claim 16 wherein the cap-labeled mRNA substrate comprises poly(A).

21. The kit of claim 20 further comprising means for stimulating decapping the cap labeled mRNA substrate.

22. The kit of claim 20 further comprising a cold poly(A) competitor RNA.

23. The kit of claim 16 wherein the cap-labeled nRNA substrate comprises an RNA element.

24. The kit of claim 23 wherein the RNA element is an AU-rich element.

25. The kit of claim 24 further comprising means for reducing decapping the cap-labeled mRNA substrate.

26. The kit of claim 24 further comprising an AU-rich element competitor RNA.

27. A mammalian in vitro mRNA decapping system comprising:
   a) a polysome-free HeLa cell cytoplasmic extract;
   b) a cap-labeled mRNA substrate; and
   c) means for decapping the cap-labeled mRNA substrate.

28. The kit of claim 27 wherein the polysome-free HeLa cell cytoplasmic extract is a HeLa S100 cell cytoplasmic extract.

29. A kit for measuring mRNA decapping in vitro comprising:
   a) a polysome-free HeLa cell cytoplasmic extract;
   b) a cap-labeled mRNA substrate; and
   c) means for decapping the cap-labeled mRNA substrate.

30. The kit of claim 29 wherein the polysome-free HeLa cell cytoplasmic extract is a HeLa S100 cytoplasmic extract.

* * * * *

UNITED STATES PATENT AND TRADEMARK OFFICE
CERTIFICATE OF CORRECTION

PATENT NO. : 6,852,531 B2
DATED : February 8, 2005
INVENTOR(S) : Wilusz et al.

It is certified that error appears in the above-identified patent and that said Letters Patent is hereby corrected as shown below:

Title page,
Item [74], *Attorney, Agent, or Firm*, should read -- Hoffmann & Baron, LLP --.

Column 4,
Line 21, should read -- The $^{7me}$ GDP product of the decapping reaction... --

Column 4,
Line 34, should read -- "After 5 min., UV cross-linking was... --.

Column 5,
Lines 29-30, should read -- ...were incubated in the in vitro... --.

Column 21,
Line 34, should read -- ...cells purified using a combination... --.

Signed and Sealed this

Twelfth Day of July, 2005

JON W. DUDAS
*Director of the United States Patent and Trademark Office*

SEQUENCE LISTING

<160> NUMBER OF SEQ ID NOS: 3

<210> SEQ ID NO 1
<211> LENGTH: 41
<212> TYPE: DNA

-continued

```
<213> ORGANISM: Artificial Sequence
<220> FEATURE:
<223> OTHER INFORMATION: described in specification page 28

<400> SEQUENCE: 1
catgattatt tattatttat ttattattta tttatttaaa c                    41

<210> SEQ ID NO 2
<211> LENGTH: 34
<212> TYPE: RNA
<213> ORGANISM: Artificial Sequence
<220> FEATURE:
<223> OTHER INFORMATION: described in specification page 29

<400> SEQUENCE: 2
auuauuuauu auuuauuuau uauuuauuua uuua                            34

<210> SEQ ID NO 3
<211> LENGTH: 33
<212> TYPE: RNA
<213> ORGANISM: Artificial Sequence
<220> FEATURE:
<223> OTHER INFORMATION: described in specification page 29

<400> SEQUENCE: 3
ggauuaacua auugauaccg cguauacacg cgg                             33
```